US011957533B2

(12) United States Patent
Shojaei et al.

(10) Patent No.: US 11,957,533 B2
(45) Date of Patent: Apr. 16, 2024

(54) ALIGNER STAGE ANALYSIS TO OBTAIN MECHANICAL INTERACTIONS OF ALIGNERS AND TEETH FOR TREATMENT PLANNING

(71) Applicant: Align Technology, Inc., San Jose, CA (US)

(72) Inventors: Iman Shojaei, San Jose, CA (US); Reza Shirazi Aghjari, San Jose, CA (US)

(73) Assignee: ALIGN TECHNOLOGY, INC., San Jose, CA (US)

( * ) Notice: Subject to any disclaimer, the term of this patent is extended or adjusted under 35 U.S.C. 154(b) by 0 days.

(21) Appl. No.: 18/108,486

(22) Filed: Feb. 10, 2023

(65) Prior Publication Data

US 2023/0293264 A1     Sep. 21, 2023

Related U.S. Application Data

(63) Continuation of application No. 17/139,222, filed on Dec. 31, 2020, now Pat. No. 11,622,836.

(60) Provisional application No. 62/956,006, filed on Dec. 31, 2019.

(51) Int. Cl.
| | | |
|---|---|---|
| G06T 19/20 | (2011.01) | |
| A61C 7/00 | (2006.01) | |
| A61C 7/08 | (2006.01) | |
| G06T 19/00 | (2011.01) | |
| G16H 20/40 | (2018.01) | |
| G16H 50/50 | (2018.01) | |

(52) U.S. Cl.
CPC ............... *A61C 7/002* (2013.01); *A61C 7/08* (2013.01); *G06T 19/00* (2013.01); *G16H 20/40* (2018.01); *G16H 50/50* (2018.01)

(58) Field of Classification Search
CPC ............ A61C 7/002; A61C 7/08; G06T 19/00
USPC .......................................................... 433/24
See application file for complete search history.

(56) References Cited

U.S. PATENT DOCUMENTS

| | | |
|---|---|---|
| 5,820,368 A | 10/1998 | Wolk |
| 6,386,864 B1 | 5/2002 | Kuo |
| 6,454,565 B2 | 9/2002 | Phan et al. |
| 6,471,511 B1 | 10/2002 | Chishti et al. |
| 6,607,382 B1 | 8/2003 | Kuo et al. |
| 6,783,604 B2 | 8/2004 | Tricca |
| 6,790,035 B2 | 9/2004 | Tricca et al. |
| 6,814,574 B2 | 11/2004 | Abolfathi et al. |
| 6,947,038 B1 | 9/2005 | Anh et al. |
| 7,074,039 B2 | 7/2006 | Kopelman et al. |
| 7,104,792 B2 | 9/2006 | Taub et al. |
| 7,121,825 B2 | 10/2006 | Chishti et al. |
| 7,160,107 B2 | 1/2007 | Kopelman et al. |

(Continued)

*Primary Examiner* — Thomas J Lett

(74) *Attorney, Agent, or Firm* — Wilson Sonsini Goodrich & Rosati

(57) ABSTRACT

Systems and methods of simulating, modeling, and validating orthodontic treatment are disclosed. The method may include designing an orthodontic treatment system or force system, generative a displacement field between a first position of a patient's teeth and a second position, modeling the three-dimensional force-displacement model generated by the treatment system or force system, and validating the treatment system or force system. The methods disclosed herein may be iterated to optimize the orthodontic force system or treatment system.

16 Claims, 14 Drawing Sheets

(56) References Cited

U.S. PATENT DOCUMENTS

| | | |
|---|---|---|
| 7,192,273 B2 | 3/2007 | McSURDY, Jr. |
| 7,347,688 B2 | 3/2008 | Kopelman et al. |
| 7,354,270 B2 | 4/2008 | Abolfathi et al. |
| 7,448,514 B2 | 11/2008 | Wen |
| 7,481,121 B1 | 1/2009 | Cao |
| 7,543,511 B2 | 6/2009 | Kimura et al. |
| 7,553,157 B2 | 6/2009 | Abolfathi et al. |
| 7,600,999 B2 | 10/2009 | Knopp |
| 7,658,610 B2 | 2/2010 | Knopp |
| 7,766,658 B2 | 8/2010 | Tricca et al. |
| 7,771,195 B2 | 8/2010 | Knopp et al. |
| 7,854,609 B2 | 12/2010 | Chen et al. |
| 7,871,269 B2 | 1/2011 | Wu et al. |
| 7,878,801 B2 | 2/2011 | Abolfathi et al. |
| 7,878,805 B2 | 2/2011 | Moss et al. |
| 7,883,334 B2 | 2/2011 | Li et al. |
| 7,914,283 B2 | 3/2011 | Kuo |
| 7,947,508 B2 | 5/2011 | Tricca et al. |
| 8,152,518 B2 | 4/2012 | Kuo |
| 8,172,569 B2 | 5/2012 | Matty et al. |
| 8,235,715 B2 | 8/2012 | Kuo |
| 8,292,617 B2 | 10/2012 | Brandt et al. |
| 8,337,199 B2 | 12/2012 | Wen |
| 8,401,686 B2 | 3/2013 | Moss et al. |
| 8,517,726 B2 | 8/2013 | Kakavand et al. |
| 8,562,337 B2 | 10/2013 | Kuo et al. |
| 8,641,414 B2 | 2/2014 | Borovinskih et al. |
| 8,684,729 B2 | 4/2014 | Wen |
| 8,708,697 B2 | 4/2014 | Li et al. |
| 8,758,009 B2 | 6/2014 | Chen et al. |
| 8,771,149 B2 | 7/2014 | Rahman et al. |
| 8,899,976 B2 | 12/2014 | Chen et al. |
| 8,899,977 B2 | 12/2014 | Cao et al. |
| 8,936,463 B2 | 1/2015 | Mason et al. |
| 8,936,464 B2 | 1/2015 | Kopelman |
| 9,022,781 B2 | 5/2015 | Kuo et al. |
| 9,119,691 B2 | 9/2015 | Namiranian et al. |
| 9,161,823 B2 | 10/2015 | Morton et al. |
| 9,241,774 B2 | 1/2016 | Li et al. |
| 9,326,831 B2 | 5/2016 | Cheang |
| 9,433,476 B2 | 9/2016 | Khardekar et al. |
| 9,610,141 B2 | 4/2017 | Kopelman et al. |
| 9,655,691 B2 | 5/2017 | Li et al. |
| 9,675,427 B2 | 6/2017 | Kopelman |
| 9,700,385 B2 | 7/2017 | Webber |
| 9,744,001 B2 | 8/2017 | Choi et al. |
| 9,844,424 B2 | 12/2017 | Wu et al. |
| 10,045,835 B2 | 8/2018 | Boronkay et al. |
| 10,111,730 B2 | 10/2018 | Webber et al. |
| 10,150,244 B2 | 12/2018 | Sato et al. |
| 10,201,409 B2 | 2/2019 | Mason et al. |
| 10,213,277 B2 | 2/2019 | Webber et al. |
| 10,299,894 B2 | 5/2019 | Tanugula et al. |
| 10,363,116 B2 | 7/2019 | Boronkay |
| D865,180 S | 10/2019 | Bauer et al. |
| 10,449,016 B2 | 10/2019 | Kimura et al. |
| 10,463,452 B2 | 11/2019 | Matov et al. |
| 10,492,888 B2 | 12/2019 | Chen et al. |
| 10,517,701 B2 | 12/2019 | Boronkay |
| 10,537,406 B2 | 1/2020 | Wu et al. |
| 10,537,463 B2 | 1/2020 | Kopelman |
| 10,548,700 B2 | 2/2020 | Fernie |
| 10,555,792 B2 | 2/2020 | Kopelman et al. |
| 10,588,776 B2 | 3/2020 | Cam et al. |
| 10,613,515 B2 | 4/2020 | Cramer et al. |
| 10,743,964 B2 | 8/2020 | Wu et al. |
| 10,758,323 B2 | 9/2020 | Kopelman |
| 10,781,274 B2 | 9/2020 | Liska et al. |
| 10,813,720 B2 | 10/2020 | Grove et al. |
| 10,874,483 B2 | 12/2020 | Boronkay |
| 10,881,487 B2 | 1/2021 | Cam et al. |
| 10,912,629 B2 | 2/2021 | Tanugula et al. |
| 10,959,810 B2 | 3/2021 | Li et al. |
| 10,993,783 B2 | 5/2021 | Wu et al. |
| 11,026,768 B2 | 6/2021 | Moss et al. |
| 11,026,831 B2 | 6/2021 | Kuo |
| 11,045,282 B2 | 6/2021 | Kopelman et al. |
| 11,045,283 B2 | 6/2021 | Riley et al. |
| 11,103,330 B2 | 8/2021 | Webber et al. |
| 11,123,156 B2 | 9/2021 | Cam et al. |
| 11,154,382 B2 | 10/2021 | Kopelman et al. |
| 11,166,788 B2 | 11/2021 | Webber |
| 11,174,338 B2 | 11/2021 | Liska et al. |
| 11,219,506 B2 | 1/2022 | Shanjani et al. |
| 11,259,896 B2 | 3/2022 | Matov et al. |
| 11,273,011 B2 | 3/2022 | Shanjani et al. |
| 11,278,375 B2 | 3/2022 | Wang et al. |
| 11,318,667 B2 | 5/2022 | Mojdeh et al. |
| 11,331,166 B2 | 5/2022 | Morton et al. |
| 11,344,385 B2 | 5/2022 | Morton et al. |
| 11,376,101 B2 | 7/2022 | Sato et al. |
| 11,419,702 B2 | 8/2022 | Sato et al. |
| 11,419,710 B2 | 8/2022 | Mason et al. |
| 11,471,253 B2 | 10/2022 | Venkatasanthanam et al. |
| 11,497,586 B2 | 11/2022 | Kopelman |
| 11,504,214 B2 | 11/2022 | Wu et al. |
| 11,523,881 B2 | 12/2022 | Wang et al. |
| 11,534,268 B2 | 12/2022 | Li et al. |
| 11,534,974 B2 | 12/2022 | O'Leary et al. |
| 11,554,000 B2 | 1/2023 | Webber |
| 11,564,777 B2 | 1/2023 | Kopelman et al. |
| 11,571,278 B2 | 2/2023 | Kopelman et al. |
| 11,571,279 B2 | 2/2023 | Wang et al. |
| 11,576,750 B2 | 2/2023 | Kopelman et al. |
| 11,576,752 B2 | 2/2023 | Morton et al. |
| 11,589,955 B2 | 2/2023 | Medvinskaya et al. |
| 11,596,502 B2 | 3/2023 | Webber et al. |
| 11,602,414 B2 | 3/2023 | Sato et al. |
| 11,642,194 B2 | 5/2023 | Boronkay et al. |
| 11,642,198 B2 | 5/2023 | Kopelman et al. |
| 11,666,415 B2 | 6/2023 | Wang et al. |
| 11,701,203 B2 | 7/2023 | Svetlana et al. |
| 11,737,857 B2 | 8/2023 | Mitra et al. |
| 11,779,243 B2 | 10/2023 | Huizhong et al. |
| 11,779,437 B2 | 10/2023 | Cam et al. |
| 11,793,606 B2 | 10/2023 | Cam et al. |
| 2002/0192617 A1 | 12/2002 | Phan et al. |
| 2004/0166462 A1 | 8/2004 | Phan et al. |
| 2004/0166463 A1 | 8/2004 | Wen et al. |
| 2005/0014105 A1 | 1/2005 | Abolfathi et al. |
| 2005/0186524 A1 | 8/2005 | Abolfathi et al. |
| 2005/0244768 A1 | 11/2005 | Taub et al. |
| 2006/0019218 A1 | 1/2006 | Kuo |
| 2006/0078841 A1 | 4/2006 | Desimone et al. |
| 2006/0115782 A1 | 6/2006 | Li et al. |
| 2006/0115785 A1 | 6/2006 | Li et al. |
| 2006/0199142 A1 | 9/2006 | Liu et al. |
| 2006/0234179 A1 | 10/2006 | Wen et al. |
| 2008/0118882 A1 | 5/2008 | Su |
| 2008/0160473 A1 | 7/2008 | Li et al. |
| 2008/0286716 A1 | 11/2008 | Sherwood |
| 2008/0286717 A1 | 11/2008 | Sherwood |
| 2009/0280450 A1 | 11/2009 | Kuo |
| 2010/0055635 A1 | 3/2010 | Kakavand |
| 2010/0129763 A1 | 5/2010 | Kuo |
| 2011/0269092 A1 | 11/2011 | Kuo et al. |
| 2014/0067334 A1 | 3/2014 | Kuo |
| 2016/0193014 A1 | 7/2016 | Morton et al. |
| 2017/0007359 A1 | 1/2017 | Avi et al. |
| 2017/0135793 A1 | 5/2017 | Webber et al. |
| 2018/0174367 A1* | 6/2018 | Marom ............... A61B 34/10 |
| 2018/0360567 A1 | 12/2018 | Xue et al. |
| 2019/0046297 A1 | 2/2019 | Kopelman et al. |
| 2019/0099129 A1 | 4/2019 | Kopelman et al. |
| 2019/0125493 A1* | 5/2019 | Salah ............... G16H 50/70 |
| 2019/0262101 A1 | 8/2019 | Shanjani et al. |
| 2019/0298494 A1 | 10/2019 | Webber et al. |
| 2020/0155276 A1 | 5/2020 | Bruce et al. |
| 2020/0188062 A1 | 6/2020 | Kopelman et al. |
| 2021/0147672 A1 | 5/2021 | Cole et al. |

* cited by examiner

ALIGNER STAGE ANALYSIS TO OBTAIN MECHANICAL INTERACTIONS OF ALIGNERS AND TEETH FOR TREATMENT PLANNING

CROSS-REFERENCE

This application is a continuation of U.S. patent application Ser. No. 17/139,222, filed Dec. 31, 2020, which claims the benefit of U.S. Provisional Application No. 62/956,006, filed Dec. 31, 2019, the disclosures of which are incorporated herein by reference in their entirety.

BACKGROUND

The field of orthodontic treatment often includes addressing issues with malpositioned teeth and/or jaws. The field may include diagnosis, prevention, and/or correction of malocclusions. A person seeking orthodontic treatment may seek a treatment plan from an orthodontist, such as a professional who has undergone special training after graduating from dental school. Many orthodontic treatment plans include treatment with braces, brackets, wires, and/or polymeric appliances. A person seeking orthodontic treatment may have orthodontic appliances adjusted at various times by an orthodontic professional who designs and/or implements the orthodontic appliances.

An orthodontic appliance may be designed by using a physical force measurement apparatus to estimate mechanical interactions between a patient's teeth and a sample orthodontic appliance and adjusting the design of the orthodontic appliance based on the estimated mechanical interactions. Alternatively, an orthodontic appliance may be designed by using finite element analysis to solve the mechanical interactions between the patient's teeth and the orthodontic appliance. However, finite element analysis is computationally expensive and time-intensive and is therefore not well-adapted for orthodontic treatment planning.

SUMMARY

This disclosure generally relates to systems, methods, and/or computer-readable media related to simulating orthodontic treatment of a patient's teeth, and particularly to simulate mechanical interactions of aligners and teeth to model and verify force applications. The implementations herein provide a computationally effective way to model mechanical interactions between aligners and a patient's teeth throughout the stages of a treatment plan. In some aspects, the methods herein use spatial differences between an aligner and a patient's teeth to model a displacement field. The displacement field may provide the basis for a 3-dimensional (3D) force-displacement model. For example, the methods described herein may enable the prediction of mechanical interactions between the aligner and the patient's teeth from a direct computer-implemented solution. As noted herein, the implementations described use a computationally efficient solution to replace existing finite element analysis methods to improve computation times and increase precision and function of dental aligner systems. The implementations herein also enable the rapid, iterative design and optimization of an orthodontic force system or orthodontic treatment plan, for example an appliance system or an aligner system.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION

Figure 1:
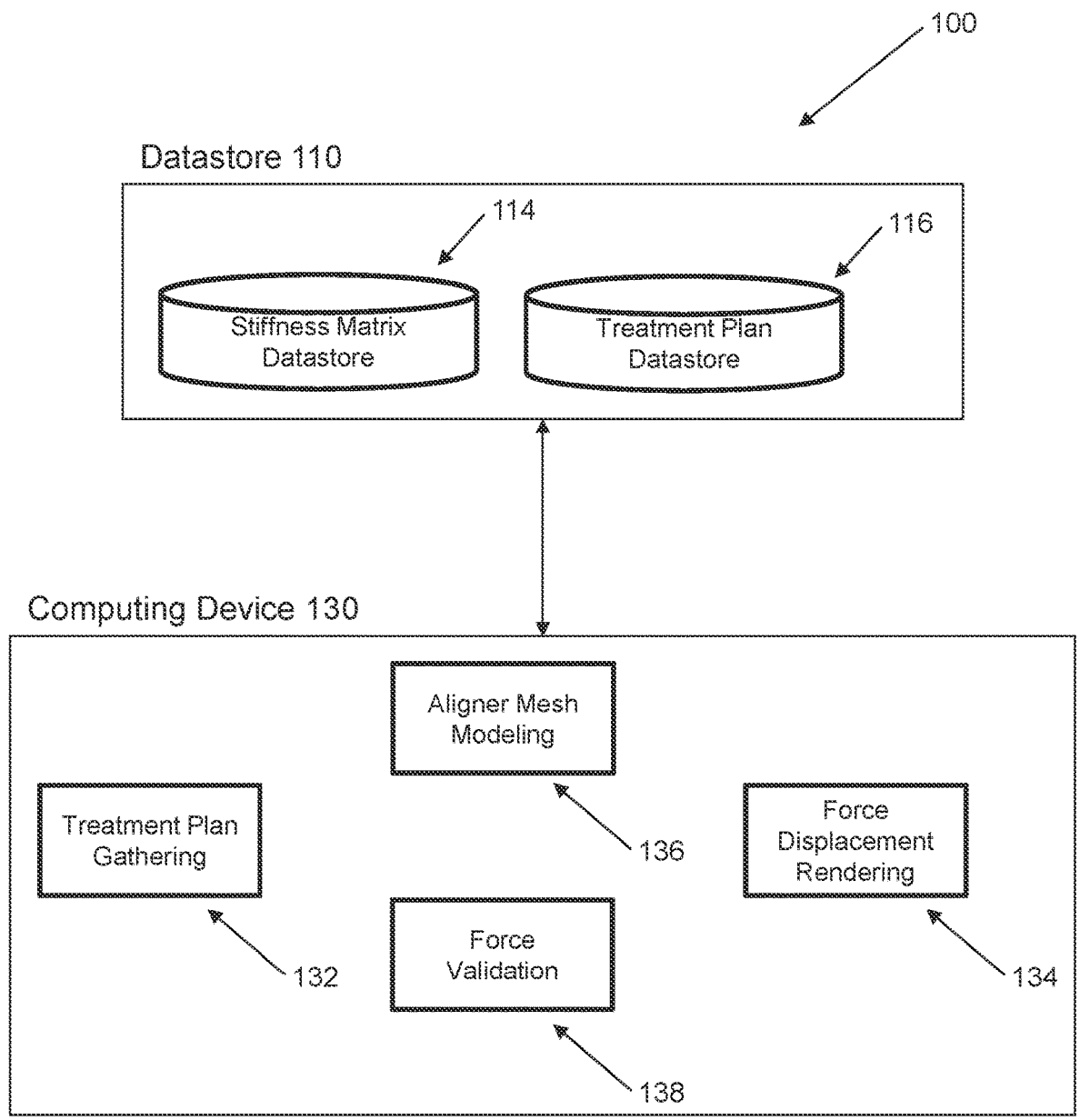
FIG. 1 depicts an example of one or more of the elements of the estimated orthodontic treatment simulation system, in accordance with one or more embodiments herein.

A better understanding of the features and advantages of the present disclosure will be obtained by reference to the following detailed description that sets forth illustrative embodiments, in which the principles of embodiments of the present disclosure are utilized, and the accompanying drawings.

Although the detailed description contains many specifics, these should not be construed as limiting the scope of the disclosure but merely as illustrating different examples and aspects of the present disclosure. It should be appreciated that the scope of the disclosure includes other embodiments not discussed in detail above. Various other modifications, changes and variations which will be apparent to those skilled in the art may be made in the arrangement, operation and details of the methods, systems, and apparatus of the present disclosure provided herein without departing from the spirit and scope of the invention as described herein.

As used herein the terms "dental appliance," and "tooth receiving appliance" are treated synonymously. As used herein, a "dental positioning appliance" or an "orthodontic appliance" may be treated synonymously, and may include any dental appliance configured to change the position of a patient's teeth in accordance with a plan, such as an orthodontic treatment plan. A "patient," as used herein may include any person, including a person seeking dental/orthodontic treatment, a person undergoing dental/orthodontic treatment, and a person who has previously undergone dental/orthodontic treatment. A "patient" may include a customer or a prospective customer of orthodontic treatment. A "dental positioning appliance" or "orthodontic appliance," as used herein, may include a set of dental appliances configured to incrementally change the position of a patient's teeth over time. As noted herein, dental positioning appliances and/or orthodontic appliances may comprise polymeric appliances configured to move a patient's teeth in accordance with an orthodontic treatment plan, for example an orthodontic aligner. The terms "appliance" and "aligner" are used interchangeably herein.

As used herein the term "and/or" may be used as a functional word to indicate that two words or expressions are to be taken together or individually. For example, the phrase "A and/or B" encompasses A alone, B alone, and A and B together. Depending on context, the term "or" need not exclude one of a plurality of words/expressions. As an example, the phrase "A or B" need not exclude A and B together.

As used herein the terms "torque" and "moment" are treated synonymously.

As used herein a "moment" may encompass a force acting on an object such as a tooth at a distance from a center of resistance. The moment may be calculated with a vector cross product of a vector force applied to a location corresponding to a displacement vector from the center of resistance, for example. The moment may comprise a vector pointing in a direction. A moment opposing another moment may encompass one of the moment vectors oriented toward a first side of the object such as the tooth and the other moment vector oriented toward an opposite side of the object such as tooth, for example. Any discussion herein referring to application of forces on a patient's teeth is equally applicable to application of moments on the teeth, and vice-versa.

As used herein a "plurality of teeth" may encompass two or more teeth. A plurality of teeth may, but need not, comprise adjacent teeth. In some embodiments, one or more posterior teeth comprises one or more of a molar, a premolar or a canine, and one or more anterior teeth comprising one or more of a central incisor, a lateral incisor, a cuspid, a first bicuspid or a second bicuspid.

The embodiments disclosed herein may be well suited for moving one or more teeth of the first group of one or more teeth or moving one or more of the second group of one or more teeth, and combinations thereof.

The embodiments disclosed herein may be well suited for combination with one or more commercially available tooth moving components such as attachments and polymeric shell appliances. In some embodiments, the appliance and one or more attachments are configured to move one or more teeth along a tooth movement vector comprising six degrees of freedom, in which three degrees of freedom are rotational and three degrees of freedom are translation.

The present disclosure provides for simulating mechanical interactions of aligners and teeth and related systems, methods, and devices. Repositioning of teeth may be accomplished with the use of a series of removable elastic positioning appliances, or aligners, such as the Invisalign® system available from Align Technology, Inc., the assignee of the present disclosure. Such appliances may have a thin shell of elastic material that generally conforms to a patient's teeth but is slightly out of alignment with an initial or immediately prior tooth configuration. Placement of the appliance over the teeth applies controlled forces in specific locations to gradually move the teeth into the new configuration. Repetition of this process with successive appliances, or aligners, comprising new configurations eventually moves the teeth through a series of intermediate configurations or alignment patterns to a final desired configuration. Repositioning of teeth may be accomplished through other series of removable orthodontic and/or dental appliances, including polymeric shell appliances.

Although reference is made to an appliance comprising a polymeric shell appliance, the embodiments disclosed herein are well suited for use with many appliances that receive teeth, for example appliances without one or more of polymers or shells. The appliance can be fabricated with one or more of many materials such as metal, glass, reinforced fibers, carbon fiber, composites, reinforced composites, aluminum, biological materials, and combinations thereof for example. The appliance can be shaped in many ways, such as with thermoforming or direct fabrication as described herein, for example. Alternatively or in combination, the appliance can be fabricated with machining such as an appliance fabricated from a block of material with computer numeric control machining. Additionally, though reference is made herein to orthodontic appliances, at least some of the techniques described herein may apply to restorative and/or other dental appliances, including without limitation crowns, veneers, teeth-whitening appliances, teeth-protective appliances, etc.

Described herein are methods and systems for planning and implementing orthodontic treatment, as well as methods and systems for accurately predicting the results of a planned orthodontic treatment system, in accordance with embodiments of the present disclosure. In some embodiments, an appliance geometry is determined in order to achieve a desired movement path to move one or more teeth from an initial arrangement to a target arrangement. In some embodiments, one or more forces applied by the appliance are verified using a force validation method disclosed herein. In some embodiments, the appliance geometry is modified based on the results of the force validation method prior to appliance fabrication.

First referencing FIG. 1, FIG. 1 shows an example of one or more of the elements of the dental treatment simulation system 100, in accordance with some embodiments. The dental treatment simulation system may comprise specialized hardware and software modules in communication with one another, including one or more datastores 110, and one or more computing devices 130. The datastore 110 of FIG. 1 may include a stiffness matrix datastore 114, and a treatment plan datastore 116. The dental treatment simulation system further comprises a specialized computing device 130 configured to collect patient data, implement one or more a machine learning algorithms, such as a convoluted neural network, and render the data for viewing. The computing device may include a treatment plan gathering device 132, a force displacement rendering engine 134, an aligner mesh modeling engine 136, and a force validation engine 138. The hardware components of the specialized computing device are described in more detail with respect to FIG. 12.

The aligner mesh modeling engine 136 models 3D images of a patient's teeth and or 3D models of aligners as 3D mesh models composed of elements and nodes. Nodes may be the corners of each element, and each element may have a polygonal shape, for example a triangle or a quadrilateral. The nodes and elements define a simplified 3D model of the patient's teeth or the aligner which may be subsequently used, for example, to determine or validate mechanical interactions between the aligner and the patient's teeth using the force validation engine 138. The modeled 3D image of the patient's teeth may be based on a collected image of the patient's teeth. Collected images of the patient's teeth may be collected using the treatment plan gathering device 132, such as a 3D scanner or a two-dimensional (2D) imaging device, such as a camera. For example, the treatment plan gathering device may comprise a camera 1525, a scanner 1520, or casts 1521, with reference to FIG. 12. The 3D models may be subsequently rendered on a screen for viewing using the force displacement rendering engine 134.

The force validation engine 138 determines one or more forces required to achieve the tooth positions and orientations determined from, for example, the treatment plan datastore 116 and one or more forces produced by an orthodontic appliance fabricated to move teeth toward the determined tooth positions and orientations. The forces to achieve said tooth positions and orientations may be determined relative to an initial tooth position of a patient. The initial tooth position may be determined, for example, using a treatment plan gathering device 132, such as a 3D scanner, a cast, or a camera. The force validation engine simulates forces using stiffness parameters retrieved from the stiffness matrix datastore 114. Forces may be simulated by a machine learning algorithm, such as a convoluted neural network. Based on the simulated forces, the tooth positions and orientations may be adjusted in the aligner mesh modeling engine 136. The adjusted forces resulting from the adjusted tooth positions and orientations may be validated using the force validation engine. This process of tooth position adjustment and force validation may be iterated until the forces meet desired specifications and a final arch is generated. The force validation engine is further discussed with respect to, for example, FIG. 2-FIG. 8.

The force displacement rendering engine 134 renders the displacement fields between a 3D model of the patient's teeth and an aligner mesh model, or between a first the aligner mesh model and a second the aligner mesh model, or between a patient's teeth in a first position and a patient's teeth in a second position. The force displacement rendering engine 134 also renders the 3D force models between the 3D model of the patient's teeth and the aligner mesh model, as determined, for example, by the aligner mesh modeling engine 136 and, in particular, the force validation engine 138 therein. The rendered 3D force models and/or displacement fields may be rendered, for example, on a screen for viewing by a patient or a dental professional. The rendered 3D force models may be used to modify a treatment plan or an aligner mesh model.

Figure 2:
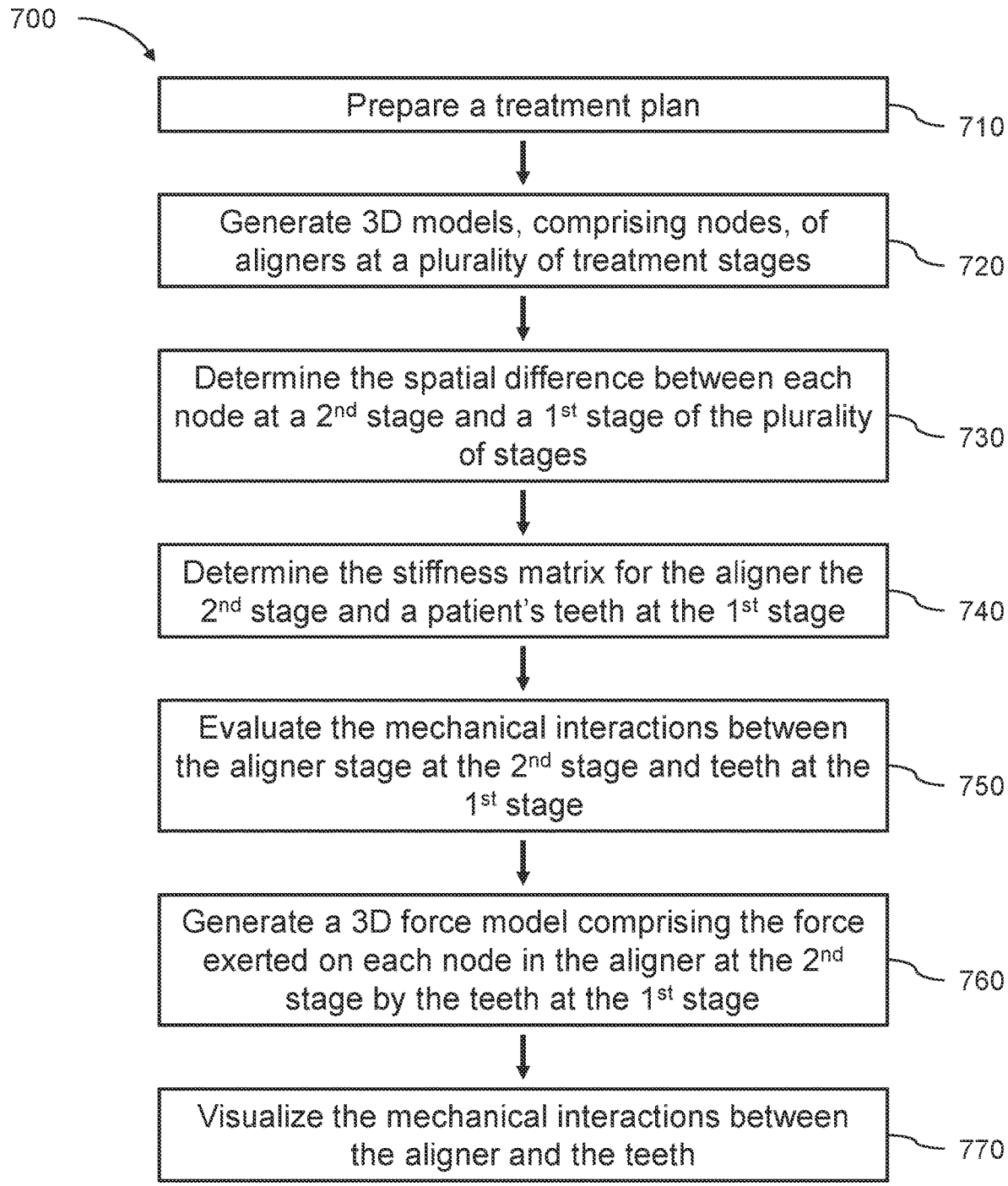
FIG. 2 illustrates a method of validating an orthodontic treatment plan, in accordance with one or more embodiments herein.

FIG. 2 describes a method 700 of validating an orthodontic treatment plan. Validation may be performed as part of method 600, with respect to FIG. 11, wherein an orthodontic treatment system is planned. In particular, method 700 may be implemented between treatment stage generation at block 620 and appliance fabrication at block 630. Method 600 is described in greater detail elsewhere herein. Returning to FIG. 2, at block 710 of method 700 a treatment plan is prepared. The treatment plan may be prepared as described in method 600, in particular at block 610, where a digital representation of a patient's teeth is received, and block 620. Treatment plan validation can be performed using various elements of system 100, with respect to FIG. 1. For example, the treatment plan at block 710 may retrieved from the treatment plan datastore 116 and/or obtained using a treatment plan gathering device 132. Block 720 may be performed using the aligner mesh modeling engine 136. Blocks 730, 740, 750, and 760 may be performed using the force validation engine 138. Block 770 may be performed using the force displacement rendering engine 134.

In block 720, 3D models of aligners at a plurality of treatment stages are generated. The plurality of treatment stages may comprise the orthodontic appliances described in method 500 elsewhere herein, with respect to FIG. 10. A treatment stage may comprise an aligner as shown and described subsequently in FIG. 9A and FIG. 9B. Each 3D model may be generated by identifying nodes of a mesh model of the aligner. Nodes may include corners of each element of the mesh. Each element of the mesh may be a polygon shape, for example a triangle or a quadrilateral. Generation of the 3D aligner mesh model is described at block 1021, with respect to FIG. 6A.

Figure 3:
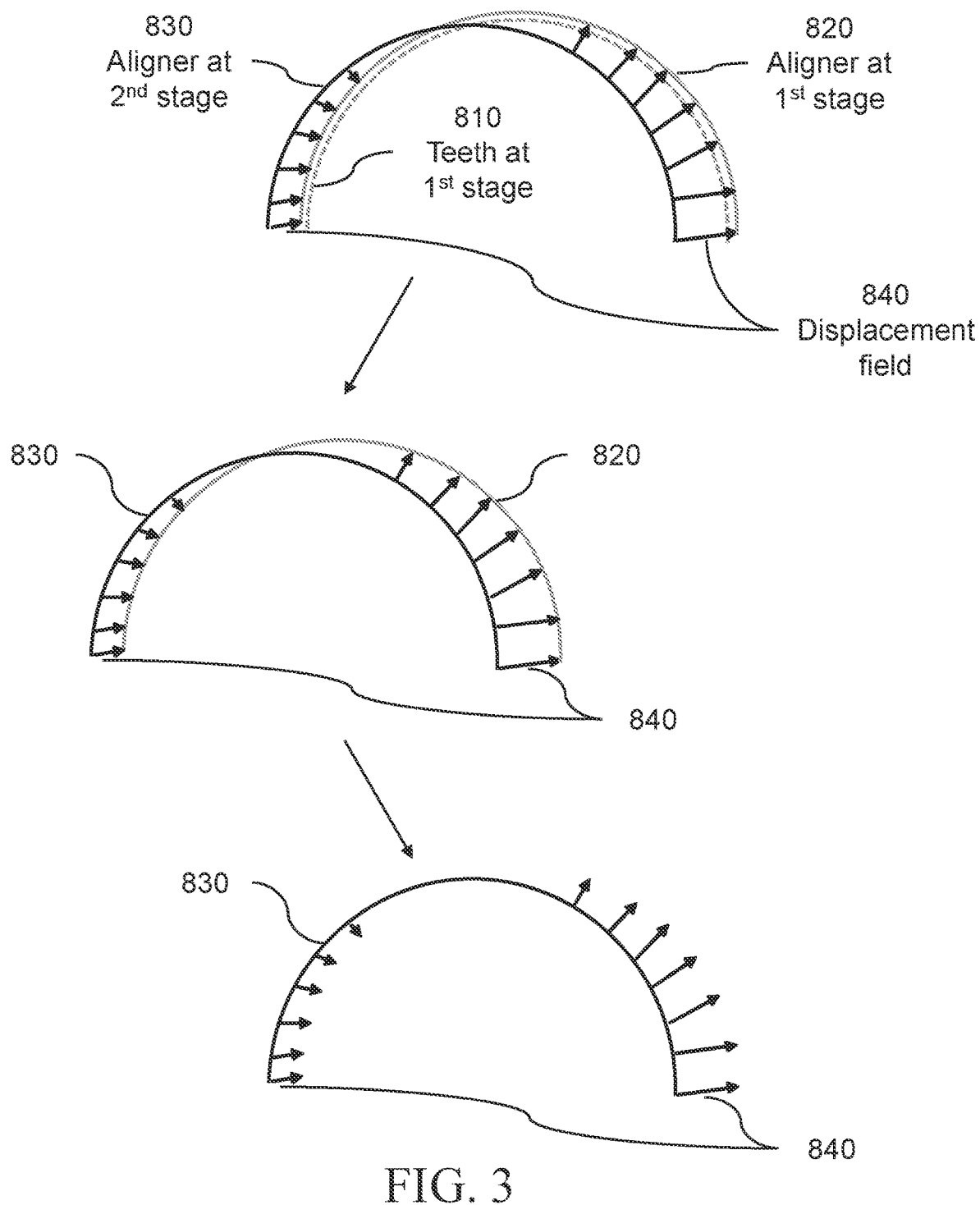
FIG. 3 depicts a displacement field between two aligner stages, in accordance with one or more embodiments herein.

In block 730, the spatial difference between each node of a first stage and a second stage of the plurality of treatment stages is determined. The first stage and the second stage may be consecutive stages in the treatment plan or they may be non-consecutive stages of the treatment plan. In some embodiments, the first stage and the second stage are an initial stage and a final stage, respectively. The spatial differences of the nodes may be represented as a displacement field, as shown in FIG. 3. The aligner at the first stage 820 may be in the same position as a patient's teeth at the first stage 810. In some embodiments, the displacement field 840 is modeled between the aligner at the first stage 820 and the aligner at the second stage 830. In some embodiments, the displacement field 840 is modeled between the patient's teeth at the first stage 810 and the aligner at the second stage 830. In some embodiments, the displacement field is modeled between the patient's teeth at the first stage and the patient's teeth at a target position or a final position representing a position following orthodontic treatment. The displacement field may be rendered, for example, using the force displacement rendering engine 134, with respect to FIG. 1, on a screen for viewing by a patient or dental professional.

In block 740 a first stiffness matrix for the patient's teeth and the first stage and a second stiffness matrix for the aligner at the second stage are determined. For example, the stiffness matrix may be a 9×9 matrix, or the stiffness matrix may be a 12×12 matrix. The stiffness matrices may be stored in and/or retrieved from the stiffness matrix datastore 114, with respect to FIG. 1. In some embodiments, the aligner stiffness matrix is derived from the aligner model. In some embodiments, the stiffness matrix is determined from material properties of the aligner or the patient's teeth. The stiffness matrices may account for a non-linear force-displacement relationship of the material. Block 740 may be performed before or after block 730 or may be performed before block 720 or 710. Stiffness matrices may be determined from historic cases and may be stored in or retrieved from the stiffness matrix datastore 114 at any point prior to block 750.

At block 750, mechanical interactions between the aligner at the second stage and the patient's teeth at the first stage are evaluated. The mechanical interactions may be determined by multiplication of displacement elements of the displacement field and stiffness elements of the stiffness matrix. For example, the mechanical interactions may be determined from the equation $F_e = k_e D_e$, where $F_e$ represents the force on each element or node of the aligner model, $k_e$ represents the stiffness at each element or node between the aligner model and the patient's teeth, and $\Delta_e$ represents the displacement between each element or node of the aligner or the patient's teeth at the first stage and the aligner or the patient's teeth at the second stage. A 3D model of the patient's teeth may be obtained from a 3D scan, for example, using a treatment plan gathering device 132, with respect to FIG. 1.

A 3D force model is generated at block 760, the 3D force model comprising the forces exerted on each node in the aligner at the second stage by the patient's teeth at the first stage. The 3D force model may be obtained using the aligner mesh modeling engine 136, with respect to FIG. 1. In some embodiments, a node is shared by two or more adjacent elements. The force exerted on a node shared by two or more elements may be determined by the vector summation of all the forces from the corresponding elements on the node. The 3D force model may comprise the forces exerted by each tooth of the patient's teeth at the first stage on the aligner at the second stage. The force on each tooth may be determined by the vector summation of all the forces exerted by all the nodes of the region of the mesh model corresponding to the tooth.

The 3D force model may be visualized at block 770. For example, the 3D force model may be rendered using the force displacement rendering engine 134, with respect to FIG. 1. The 3D force model may be viewed on a screen by a patient or a dental professional. The 3D force model may be stored for later use, for example in the treatment plan datastore 116. The 3D force model may be used by treatment planning software to evaluate directions and magnitudes of forces to be applied to the patient's teeth. Further details about the use of the 3D force model by the treatment planning software are described with respect to FIG. 4-FIG. 8.

Figure 4:
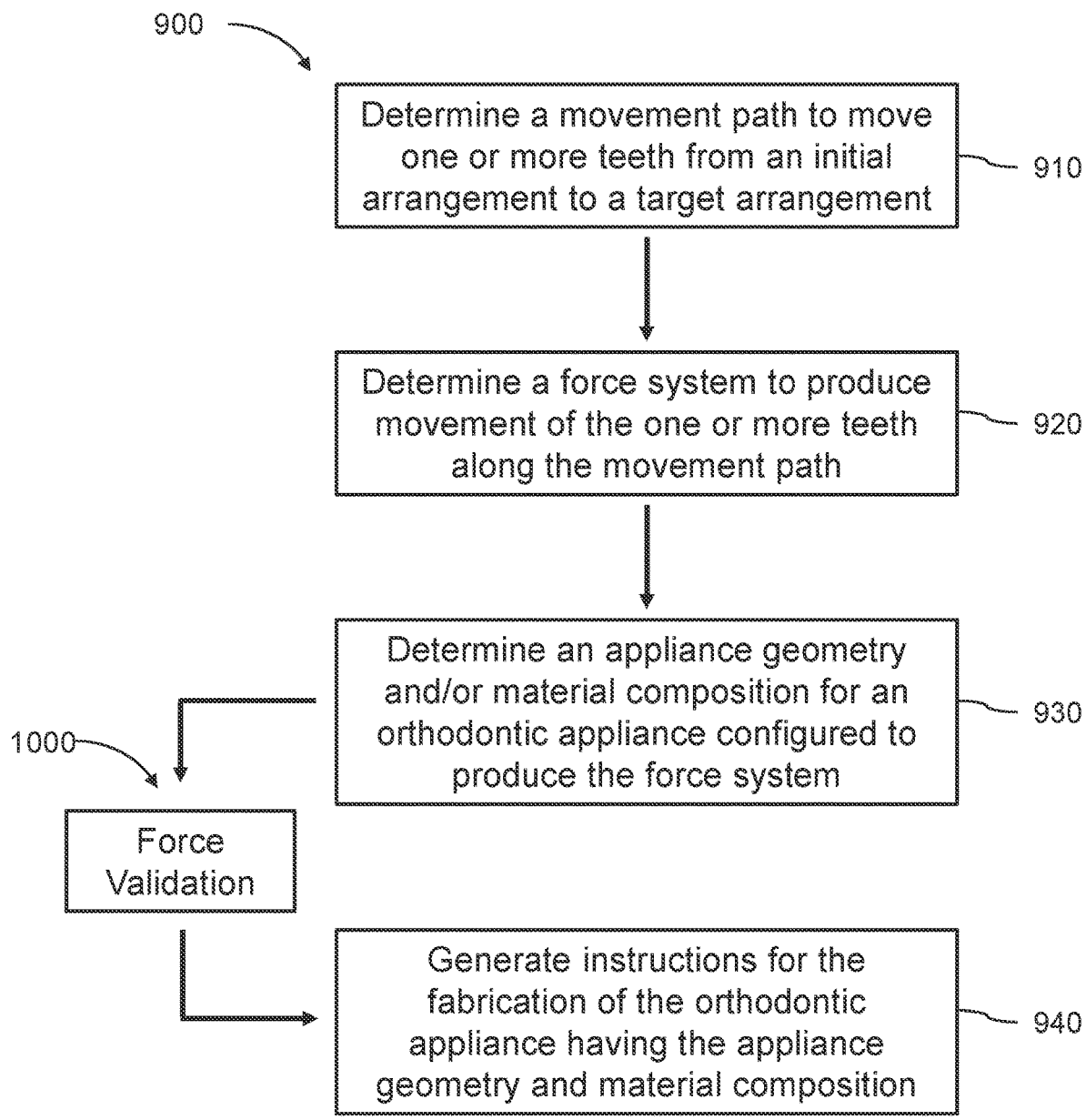
FIG. 4 illustrates a method for designing an orthodontic appliance, in accordance with one or more embodiments herein.

FIG. 4 illustrates a method 900 for designing a force system comprising one or more orthodontic appliances to be fabricated. The method comprises mapping mechanical interactions, for example, interactions between an aligner and a patient's teeth. The method 900 can be applied to any embodiment of the orthodontic appliances described herein. Some or all of the operations of the method 900 can be performed by any suitable data processing system or device, e.g., one or more processors configured with suitable instructions. For example, some or all of the operations can be performed by the computing device 130, with respect to FIG. 1.

In block 910, a movement path to move one or more teeth from an initial arrangement to a target arrangement is determined. The initial arrangement can be determined from a mold or a scan of the patient's teeth or mouth tissue, e.g., using wax bites, direct contact scanning, x-ray imaging, tomographic imaging, sonographic imaging, and other techniques for obtaining information about the position and structure of the teeth, jaws, gums and other orthodontically relevant tissue. The initial arrangement may be determined using a 3D image obtained using a treatment plan gathering device 132, with respect to FIG. 1. From the obtained data, a digital data set can be derived that represents the initial (e.g., pretreatment) arrangement of the patient's teeth and other tissues. The digital data set representing the initial arrangement may be modeled as a 3D mesh model using, for example, the aligner mesh modeling engine 136, and subsequently displayed using the force displacement rendering engine 134, with respect to FIG. 1. Optionally, the initial digital data set is processed to segment the tissue constituents from each other. For example, data structures that digitally represent individual tooth crowns can be produced. Advantageously, digital models of entire teeth can be produced, including measured or extrapolated hidden surfaces and root structures, as well as surrounding bone and soft tissue.

The target arrangement of the teeth (e.g., a desired and intended end result of orthodontic treatment force system) can be received from a clinician in the form of a prescription, can be calculated from basic orthodontic principles, and/or can be extrapolated computationally from a clinical prescription. In some embodiments, positions and orientations of the teeth in the target arrangement may be retrieved from the treatment plan datastore 116, with respect to FIG. 1. With a specification of the desired final positions of the teeth and a digital representation of the teeth themselves, the final position and surface geometry of each tooth can be specified to form a complete model of the tooth arrangement at the desired end of treatment.

Having both an initial position and a target position for each tooth, a movement path can be defined for the motion of each tooth. In some embodiments, the movement paths are configured to move the teeth in the quickest fashion with the least amount of round-tripping to bring the teeth from their initial positions to their desired target positions. The tooth paths can optionally be segmented, and the segments can be calculated so that each tooth's motion within a segment stays within threshold limits of linear and rotational translation. In this way, the end points of each path segment can constitute a clinically viable repositioning, and the aggregate of segment end points can constitute a clinically viable sequence of tooth positions, so that moving from one point to the next in the sequence does not result in a collision of teeth.

In block 920, a force system to produce movement of the one or more teeth along the movement path is determined. A force system can include one or more forces and/or one or more torques. Different force systems can result in different types of tooth movement, such as tipping, translation, rotation, extrusion, intrusion, root movement, etc. Biomechanical principles, modeling techniques, force calculation/measurement techniques, and the like, including knowledge and approaches commonly used in orthodontia, may be used to determine the appropriate force system to be applied to the tooth to accomplish the tooth movement. In determining the force system to be applied, sources may be considered including literature, force systems determined by experimentation or virtual modeling, computer-based modeling, clinical experience, minimization of unwanted forces, etc.

Determination of the force system can be performed in a variety of ways. For example, in some embodiments, the force system is determined on a patient-by-patient basis, e.g., using patient-specific data. Alternatively or in combination, the force system can be determined based on a generalized model of tooth movement (e.g., based on experimentation, modeling, clinical data, etc.), such that patient-specific data is not necessarily used. In some embodiments, determination of a force system involves calculating specific force values to be applied to one or more teeth to produce a particular movement. The calculated forces may be stored in and/or retrieved from the treatment plan datastore 116, with respect to FIG. 1. In some embodiments, determination of a force system can be performed at a high level without calculating specific force values for the teeth. For instance, block 920 can involve determining a particular type of force to be applied (e.g., extrusive force, intrusive force, translational force, rotational force, tipping force, torqueing force, etc.) without calculating the specific magnitude and/or direction of the force.

In block 930, an appliance geometry and/or material composition for an orthodontic appliance configured to produce the force system is determined. The appliance can be any embodiment of the appliances discussed herein, such as an appliance having variable localized properties, integrally formed components, and/or power arms.

For example, in some embodiments, the appliance comprises a heterogeneous thickness, a heterogeneous stiffness, or a heterogeneous material composition. In some embodiments, the appliance comprises two or more of a heterogeneous thickness, a heterogeneous stiffness, or a heterogeneous material composition. In some embodiments, the appliance comprises a heterogeneous thickness, a heterogeneous stiffness, and a heterogeneous material composition. The heterogeneous thickness, stiffness, and/or material composition can be configured to produce the force system for moving the teeth, e.g., by preferentially applying forces at certain locations on the teeth. For example, an appliance with heterogeneous thickness can include thicker portions that apply more force on the teeth than thinner portions. As another example, an appliance with heterogeneous stiffness can include stiffer portions that apply more force on the teeth than more elastic portions. Variations in stiffness can be achieved by varying the appliance thickness, material composition, and/or degree of photopolymerization, as described herein.

In some embodiments, determining the appliance geometry and/or material composition comprises determining the geometry and/or material composition of one or more integrally formed components to be directly fabricated with an appliance shell. The integrally formed component can be any of the embodiments described herein. The geometry and/or material composition of the integrally formed component(s) can be selected to facilitate application of the force system onto the patient's teeth. The material composition of the integrally formed component can be the same as or different from the material composition of the shell.

In some embodiments, determining the appliance geometry comprises determining the geometry for a variable gable bend.

Block 930 can involve analyzing the desired force system in order to determine an appliance geometry and material composition that would produce the force system. In some embodiments, the analysis involves determining appliance properties, for example stiffness, at one or more locations that would produce a desired force at the one or more locations. The analysis can then involve determining an appliance geometry and material composition at the one or more locations to achieve the specified properties. Determination of the appliance geometry and material composition can be performed using a treatment or force application simulation environment. A simulation environment can include, e.g., computer modeling systems, biomechanical systems or apparatus, and the like. For example, the simulation environment may comprise one or more of the modules described with respect to FIG. 1. Optionally, digital models of the appliance and/or teeth can be produced, such as finite element models. The finite element models can be created using computer program application software available from a variety of vendors. For creating solid geometry models, computer aided engineering (CAE) or computer aided design (CAD) programs can be used, such as the AutoCAD® software products available from Autodesk, Inc., of San Rafael, CA For creating finite element models and analyzing them, program products from a number of vendors can be used, including finite element analysis packages from ANSYS, Inc., of Canonsburg, PA, and SIMULIA (Abaqus) software products from Dassault Systèmes of Waltham, MA.

Optionally, one or more appliance geometries and material compositions can be selected for testing or force modeling. As noted above, a desired tooth movement, as well as a force system required or desired for eliciting the desired tooth movement, can be identified. Using the simulation environment, a candidate appliance geometry and composition can be analyzed or modeled for determination of an actual force system resulting from use of the candidate appliance. One or more modifications can optionally be made to a candidate appliance, and force modeling can be further analyzed as described, e.g., in order to iteratively determine an appliance design that produces the desired force system as described with respect to FIG. 5.

Optionally, block 930 can further involve determining the geometry of one or more auxiliary components to be used in combination with the orthodontic appliance in order to exert the force system on the one or more teeth. Such auxiliaries can include one or more of tooth-mounted attachments, elastics, wires, springs, bite blocks, arch expanders, wire-and-bracket appliances, shell appliances, headgear, or any other orthodontic device or system that can be used in conjunction with the orthodontic appliances herein. The use of such auxiliary components may be advantageous in situations where it is difficult for the appliance alone to produce the force system. Additionally, auxiliary components can be added to the orthodontic appliance in order to provide other desired functionalities besides producing the force system, such as mandibular advancement splints to treat sleep apnea, pontics to improve aesthetic appearance, and so on. In some embodiments, the auxiliary components are fabricated and provided separately from the orthodontic appliance. Alternatively, the geometry of the orthodontic appliance can be modified to include one or more auxiliary components as integrally formed components.

Optionally, after block 930 but before instructing appliance fabrication at block 940, forces applied by the orthodontic appliance in the determined appliance geometry may be validated using method 1000. For example, force validation may be used to confirm that the forces exerted between the orthodontic appliances of a force system and the patient's teeth match the predicted forces, as described with respect to FIG. 5. For example, force validation may be used to determine whether the forces exerted between an orthodontic appliance of a treatment system and the patient's teeth fall within an optimal range for treatment, as described with respect to FIG. 9. The appliance geometry may subsequently be modified to achieve the predicted forces or forces within the optimal range for treatment. The force validation method 1000 for verifying the forces of a force system is discussed further with respect to FIG. 5.

In block 940, instructions for fabrication of the orthodontic appliance having the appliance geometry and material composition are generated. The instructions can be configured to control a fabrication system or device in order to produce the orthodontic appliance with the specified appliance geometry and material composition. In some embodiments, the instructions are configured for manufacturing the orthodontic appliance using direct fabrication (e.g., stereolithography, selective laser sintering, fused deposition modeling, 3D printing, continuous direct fabrication, multi-material direct fabrication, etc.). Optionally, the instructions can be configured to cause a fabrication machine to directly fabricate the orthodontic appliance with teeth receiving cavities having variable gable bends, as discussed above and herein. In alternative embodiments, the instructions can be configured for indirect fabrication of the appliance, e.g., by thermoforming.

Although the above blocks show a method 900 of designing an orthodontic appliance in accordance with some embodiments, a person of ordinary skill in the art will recognize some variations based on the teaching described herein. Some of the blocks may comprise sub-blocks. Some of the blocks may be repeated as often as desired. One or more blocks of the method 900 may be performed with any suitable fabrication system or device, such as the embodiments described herein. Some of the blocks may be optional, and the order of the blocks can be varied as desired. For instance, in some embodiments, block 920 is optional, such that block 930 involves determining the appliance geometry and/or material composition based directly on the tooth movement path rather than based on the force system, as shown in method 1200 with respect to FIG. 7 and described subsequently herein.

Figure 5:
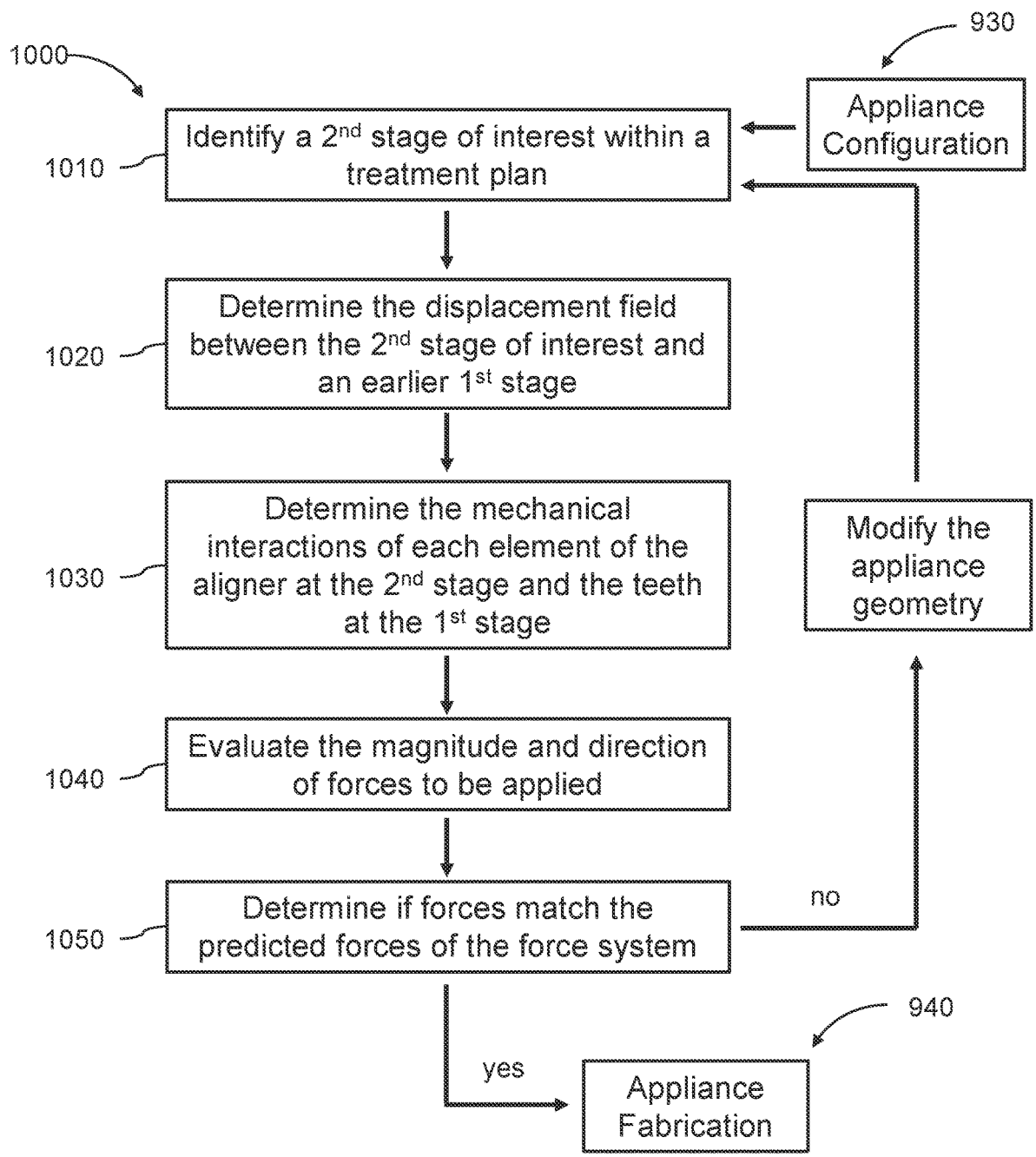
FIG. 5 illustrates a method for validating the force system of one or more orthodontic appliances designed in FIG. 4, in accordance with one or more embodiments herein.

FIG. 5 describes the force validation method 1000. Force validation may be performed using the force validation engine 138, with respect to FIG. 1. Force validation may be performed during design of the orthodontic appliance described in method 900, with respect to FIG. 4. The appliance configuration 930, for example the second aligner stage identified at block 1010, is compared to the configuration of an earlier first stage. The second aligner stage may be compared to an aligner at the first stage, or the second aligner may be compared to the patient's teeth at the first stage. The first stage and the second stage may be consecutive stages in the treatment plan or they may be non-consecutive stages of the treatment plan. In some embodiments, the first stage and the second stage are an initial stage and a final stage, respectively. A displacement field between the second stage, for example the aligner at the second stage, and the first stage, for example the patient's teeth at the first stage or the aligner at the first stage, is determined at block 1020. Additional details of the displacement field generation method 1020 are shown in FIG. 6A.

Figure 6A:
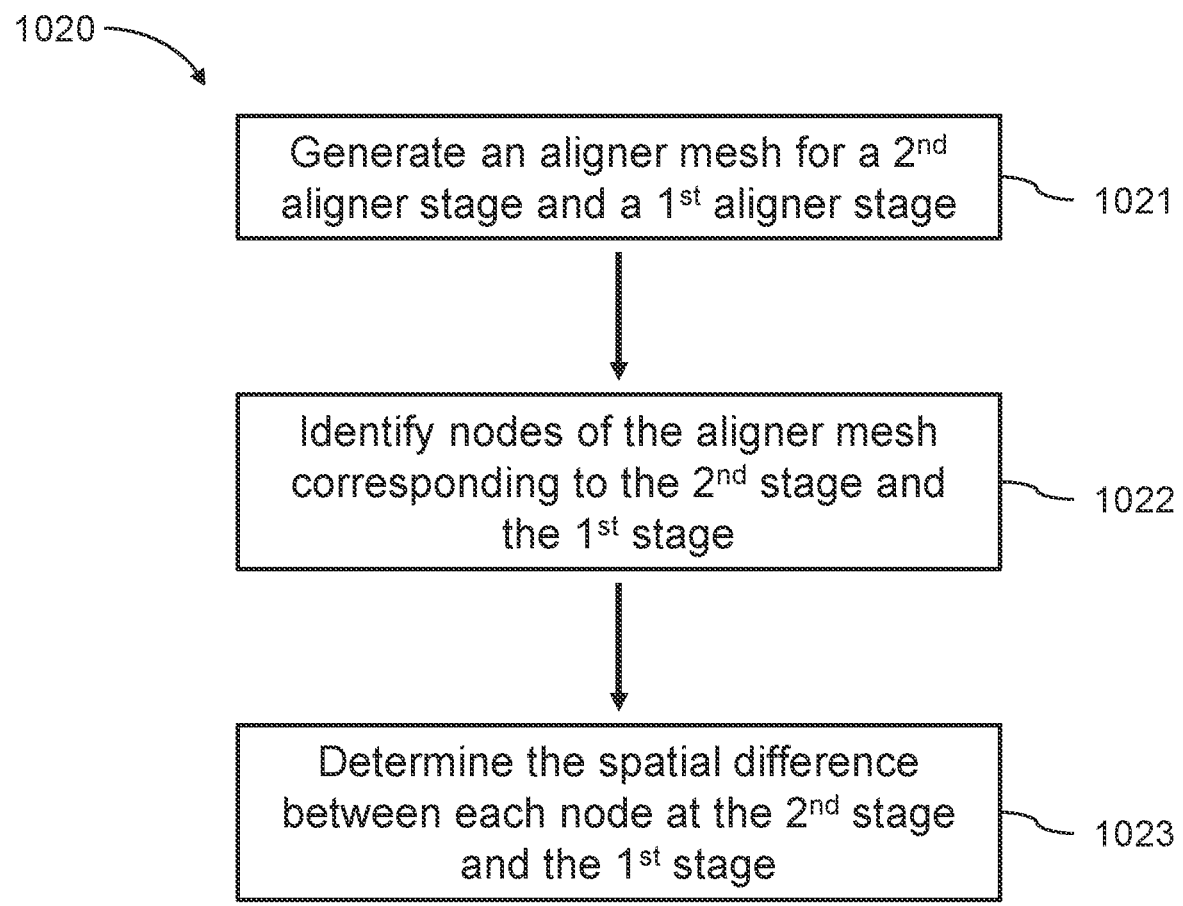
FIG. 6A illustrates a method for determining the displacement field between two stages of an orthodontic appliance designed in FIG. 4, in accordance with one or more embodiments herein.

With reference to FIG. 6A, a 3D aligner mesh may be generated for each of the first stage and the second stage at block 1021. The 3D aligner mesh may be generated using the aligner mesh modeling engine 136, with reference to FIG. 1. For example, the 3D aligner mesh may model an aligner at the first stage or the second stage, or the aligner mesh may model the patient's teeth at the first stage or the second stage. The 3D aligner mesh of each stage comprises elements, where each element of the mesh may be a polygon shape, for example a triangle or a quadrilateral. Nodes of each 3D aligner mesh are identified at block 1022. In some embodiments, the nodes may be the vertices of the elements, for example the polygon shapes, identified at block 1021. Nodes and elements may be gathered using an aligner mesh generated in treatment planning software.

A spatial difference between each node of the 3D aligner mesh at the second stage and the 3D aligner mesh at the first stage is determined at block 1023. For example, the spatial difference may be determined between the nodes of the 3D aligner mesh of the aligner at the second stage and the 3D aligner mesh of the patient's teeth at the first stage. For example, the spatial difference may be determined between the nodes of the 3D aligner mesh of the aligner at the second stage and the 3D aligner mesh of the aligner at the first stage. For example, the spatial difference may be determined between the nodes of the 3D aligner mesh of the patient's teeth at the second stage and the 3D aligner mesh of the aligner at the first stage. The displacement field is generated at block 2020 from the spatial difference between each node of the 3D aligner mesh at the second stage and each node at the first stage, with respect to FIG. 5.

Figure 6B:
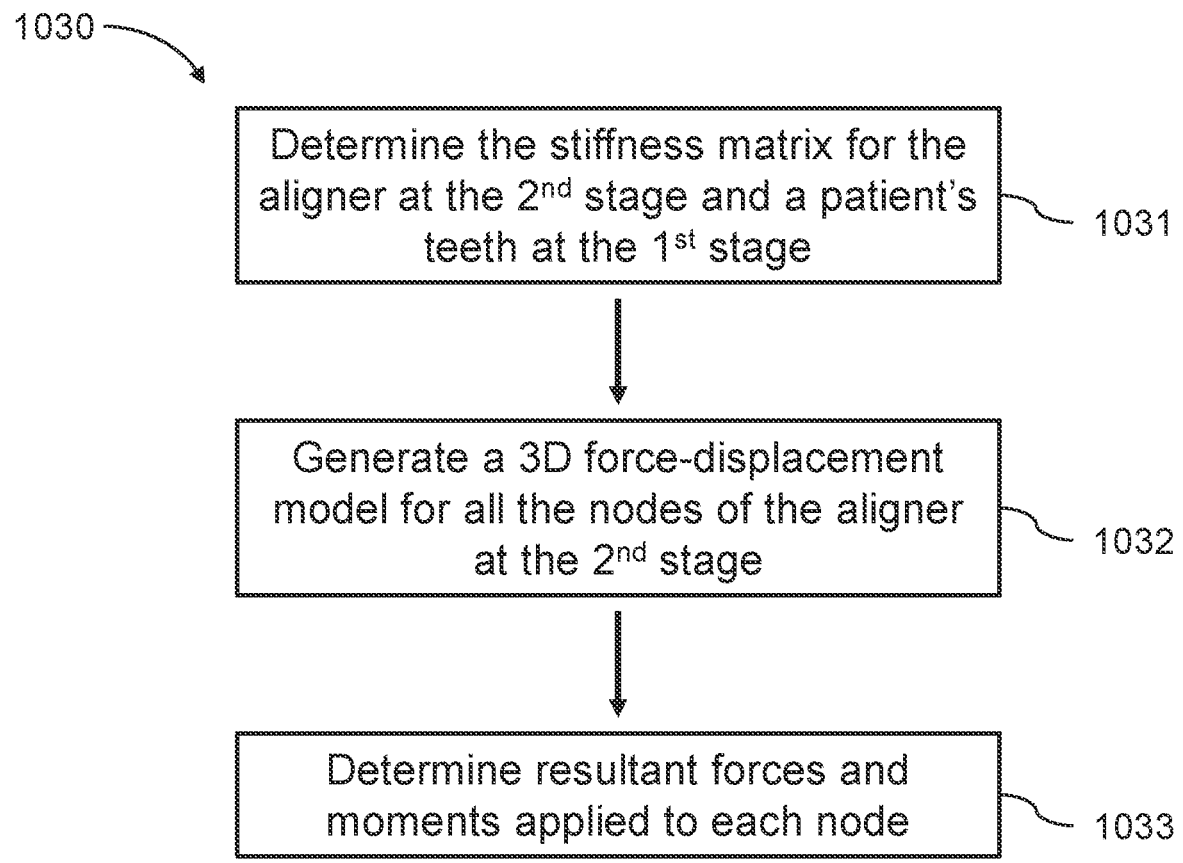
FIG. 6B illustrates a method for determining the forces between each element of an orthodontic appliance designed in FIG. 4, in accordance with one or more embodiments herein.

Returning to FIG. 5, at block 1030 mechanical interactions may be determined between each element of the aligner at the second stage and the patient's teeth at the first stage. Additional details of the mechanical interaction determination method 1030 are shown in FIG. 6B. At block 1031 at stiffness matrix is determined for the aligner at the second stage and a patient's teeth at the first stage. In some embodiments, the stiffness matrix is stored in or retrieved from the stiffness matrix datastore 114, with respect to FIG. 1. In some embodiments, the aligner stiffness matrix is derived from the aligner model. In some embodiments, the stiffness matrix is determined from material properties of the aligner or the patient's teeth. For example, the stiffness matrices may account for a non-linear force-displacement relationship of the material. For example, the elements of the stiffness matrix may be a function of the geometry of each node. For example, the elements of the stiffness matrix may be a function of material properties of the aligner. A size of the stiffness matrix may depend on a number of nodes and a number of degrees of freedom of each element in the 3D aligner mesh model. For example, an element with 3 nodes and 3 degrees of freedom may result in a 9×9 stiffness matrix. For example, an element with 4 nodes and 3 degrees of freedom may result in a 12×12 stiffness matrix.

A 3D force-displacement model is generated at block 1032. The force-displacement model may be determined for each node of the aligner at the second stage. In some embodiments, the force-displacement model is determined for each node of the patient's teeth at the first stage. The force-displacement model may be determined by multiplication of displacement elements of the displacement field and stiffness elements of the stiffness matrix. For example, the mechanical interactions may be determined from the equation $F_e = k_e \Delta_e$, where $F_e$ represents the force on each element or node of the aligner model, $k_e$ represents the stiffness at each element or node between the aligner model and the patient's teeth, and $\Delta_e$ represents the displacement between each element or node of the aligner or the patient's teeth at the first stage and the aligner or the patient's teeth at the second stage. In some embodiments, the solution of the 3D force-displacement model may involve multiplication of each element of the stiffness matrix with a matrix comprising each the displacement of each aligner element.

At block 1033, the 3D force-displacement model determined at block is applied to each node. For example, forces and moments resulting from the 3D force-displacement model are applied to each node. In some embodiments, a node is shared by two or more elements. In some embodiments, the mechanical interactions may be determined by the vector summation of all the forces from the corresponding elements on the node.

Returning to FIG. 5, at block 1040 the displacement field generated at block 1020 and the mechanical interactions determined at block 1030 may be used to evaluate the magnitude and direction of forces to be applied to the aligner at the second stage by the patient's teeth at the first stage. The forces may be compared to a predicted force generated by the force system, as shown at block 1050. If the forces determined in method 1000 match the predicted forces generated by the force generation system, for example within a pre-determined threshold, range, allowable error, or tolerance, instructions may be sent for appliance fabrication as described at block 940, with respect to FIG. 4. In some embodiments, the instructions are used to fabricate one or more appliances. In some embodiments, the instructions are stored, for example in the treatment plan datastore 116, with respect to FIG. 1. If the forces do not match the predicted forces generated by the force system, the appliance geometry may be modified and method 1000 repeated until the forces match the predicted forces. The displacement field generated at block 1020 and the 3D force model generated at block 1032, with respect to FIG. 6B, may be rendered using the force displacement rendering engine 134, with respect to FIG. 1.

Method 1000 to determine forces generated by a force system comprising one or more appliances using a displacement field and a stiffness matrix may be computationally low-cost while maintaining solution accuracy as compared to methods utilizing whole-model stiffness matrix assembly and inversion. This method may avoid an expensive contact solution and may reduce or eliminate iterative solution and/or convergence issues.

Figure 7:
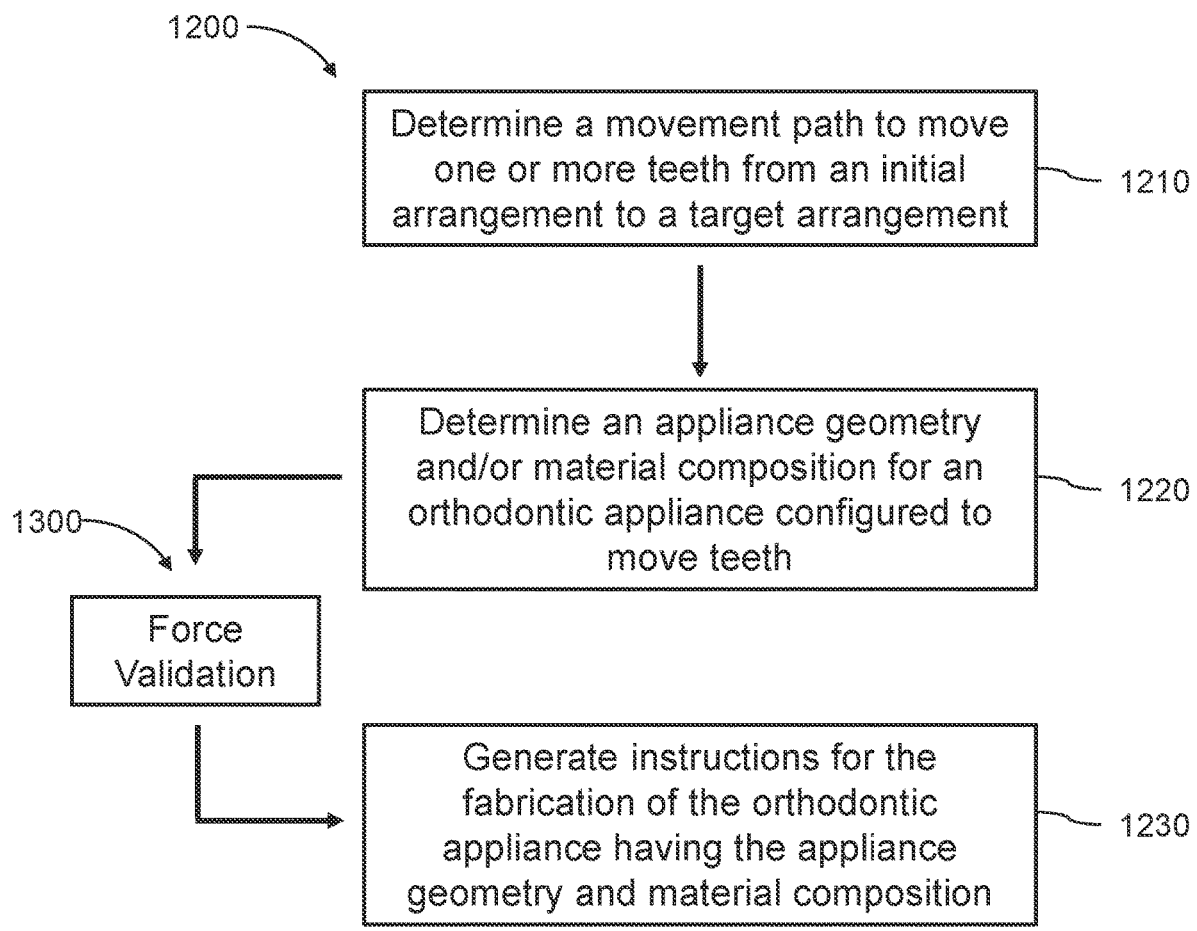
FIG. 7 illustrates a method for designing an orthodontic treatment system, in accordance with one or more embodiments herein.

FIG. 7 illustrates a method 1200 for designing one or more appliances in a treatment system to be fabricated. The method comprises mapping movements of teeth, for example a patient's teeth, and the corresponding displacements and forces. Some or all of the operations of the method 1200 can be performed by any suitable data processing system or device, e.g., one or more processors configured with suitable instructions. For example, some or all of the operations can be performed by the computing device 130, with respect to FIG. 1.

In block 1210, a movement path to move one or more teeth from an initial arrangement to a target arrangement is determined. The initial position may be determined using one or more of the methods described at block 910, with respect to FIG. 4. Digital data sets may be obtained as described at block 910. As described herein, in particular at block 910 of FIG. 4, the target arrangement of the teeth can be received from a clinician in the form of a prescription, can be calculated from basic orthodontic principles, and/or can be extrapolated computationally from a clinical prescription. The final position and surface geometry of each tooth can be specified to form a complete model of the tooth arrangement at the desired end of treatment. Having both an initial position and a target position for each tooth, a movement path can be defined for the motion of each tooth.

At block 1220, one or more appliance geometries and/or material compositions for one or more orthodontic appliances in a treatment system configured to move teeth are determined. The appliances can be any embodiment of the appliances discussed herein, such as an appliance having variable localized properties, integrally formed components, and/or power arms. In some embodiments, determining the appliance geometry and/or material composition comprises determining the geometry and/or material composition of one or more integrally formed components to be directly fabricated with an appliance shell. The integrally formed component can be any of the embodiments described herein. Block 1220 may involve analyzing the desired movement path in order to determine an appliance geometry and material composition that would produce the desired teeth movements. The analysis may involve steps disclosed herein, in particular at block 930. Optionally, one or more appliance geometries and material compositions can be selected for testing or force modeling. Optionally, block 1220 can further involve determining the geometry of one or more auxiliary components to be used in combination with the orthodontic appliance in order to exert the force system on the one or more teeth, as described at block 930.

Optionally, after block 1220 but before instructing appliance fabrication at block 1230, forces applied by the one or more orthodontic appliances in the determined appliance geometry are validated using method 1300. For example, force validation may be used to determine whether the forces exerted between the orthodontic appliance and the patient's teeth fall within an optimal range for treatment. The appliance geometry may subsequently be modified to achieve the predicted forces or forces within the optimal range for treatment. The force validation method 1300 is discussed further with respect to FIG. 8.

In block 1230, instructions for fabrication of one or more appliances of the treatment system having the appliance geometry and material composition are generated. The instructions can be configured to control a fabrication system or device in order to produce the one or more orthodontic appliance with the specified appliance geometry and material composition. The appliances may be fabricated as described herein, in particular at block 940, with respect to FIG. 4.

Figure 8:
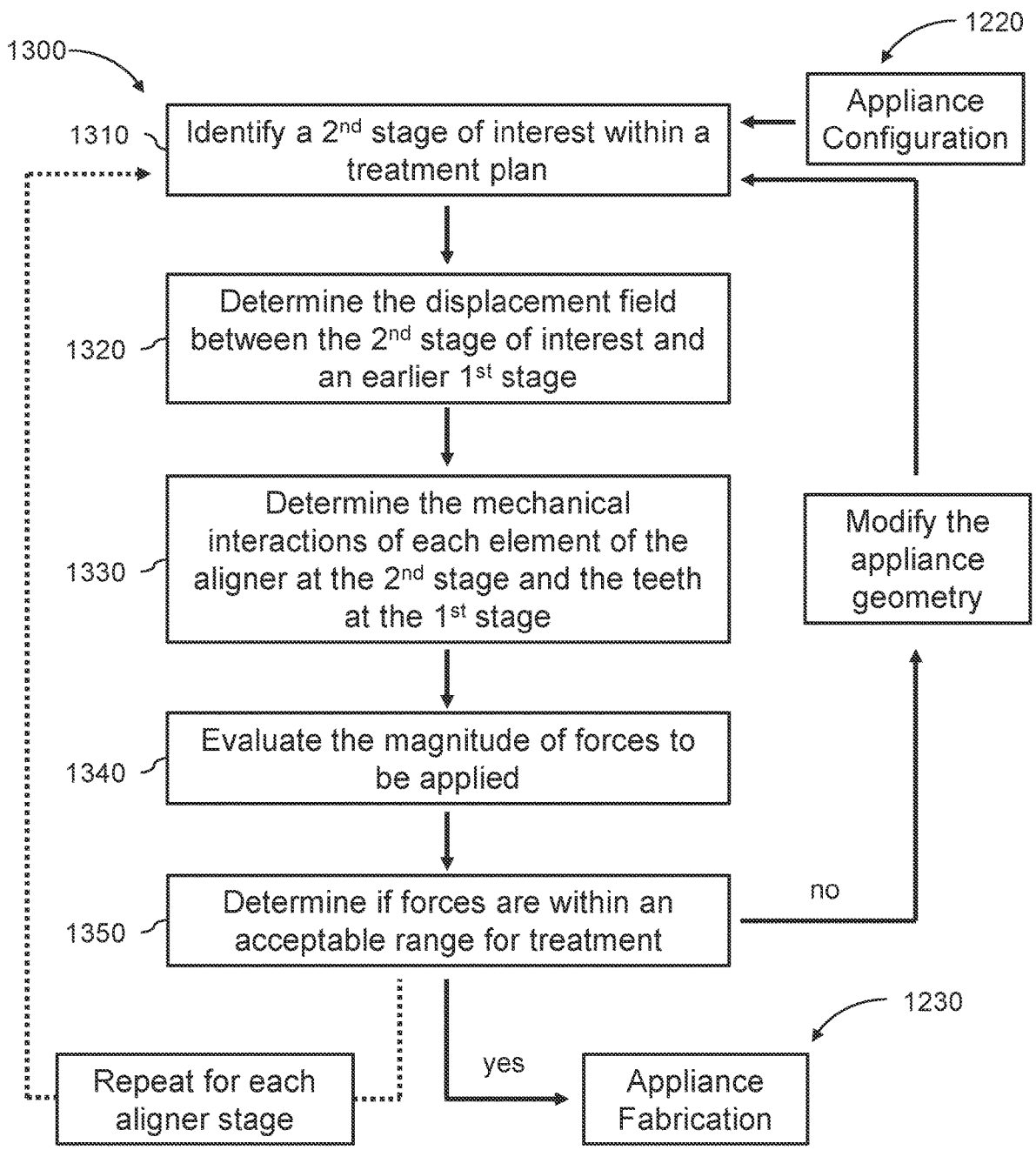
FIG. 8 illustrates a method for validating the treatment system of one or more orthodontic appliances designed in FIG. 7, in accordance with one or more embodiments herein.

FIG. 8 describes force validation method 1300. Force validation may be performed as described in method 1000, with respect to FIG. 5. The force validation method may be used to validate one or more stages of a force system. Force validation may be performed during design of the force system described in method 1200, with respect to FIG. 7. Briefly, one or more appliance configurations are identified from block 1220. A second stage of interest within the treatment plan is identified at block 1310. A displacement field may be determined between the second stage and an earlier first stage of the treatment system. The first stage and the second stage may be consecutive stages in the treatment plan or they may be non-consecutive stages of the treatment plan. In some embodiments, the first stage and the second stage are an initial stage and a final stage, respectively. The displacement field may be determined as described at block 1020, with respect to FIG. 5 and FIG. 6A.

At block 1330, mechanical interactions may be determined between each element of the aligner at the second stage and the patient's teeth at the first stage. The mechanical interactions may be determined as described at block 1230, with respect to FIG. 5 and FIG. 6B. At block 1340 the displacement field generated at block 1320 and the mechanical interactions determined at block 1330 may be used to evaluate the magnitude and direction of forces to be applied to the aligner at the second stage by the patient's teeth at the first stage. Magnitudes of the forces to be applied may be evaluated, as shown at block 1340. The forces may be compared to a minimum threshold value to determine if the force to be applied is sufficient to move teeth. The forces may be compared to a maximum threshold value to determine if the force to be applied is below a value that may cause damage or excessive pain to a patient. If the forces determined in method 1300 are within a desired range, for example above the minimum threshold value and below the maximum threshold value, instructions may be sent for appliance fabrication as described at block 1230, with respect to FIG. 7. In some embodiments, the instructions are used to fabricate one or more appliances. In some embodiments, the instructions are stored, for example in the treatment plan datastore 116, with respect to FIG. 1. If the forces determined in method 1300 are not above the minimum threshold value and below the maximum threshold value, the appliance geometry may be modified and method 1300 repeated until the forces match the predicted forces. Method 1300 may be repeated for each aligner stage of the force system.

Figure 9A:
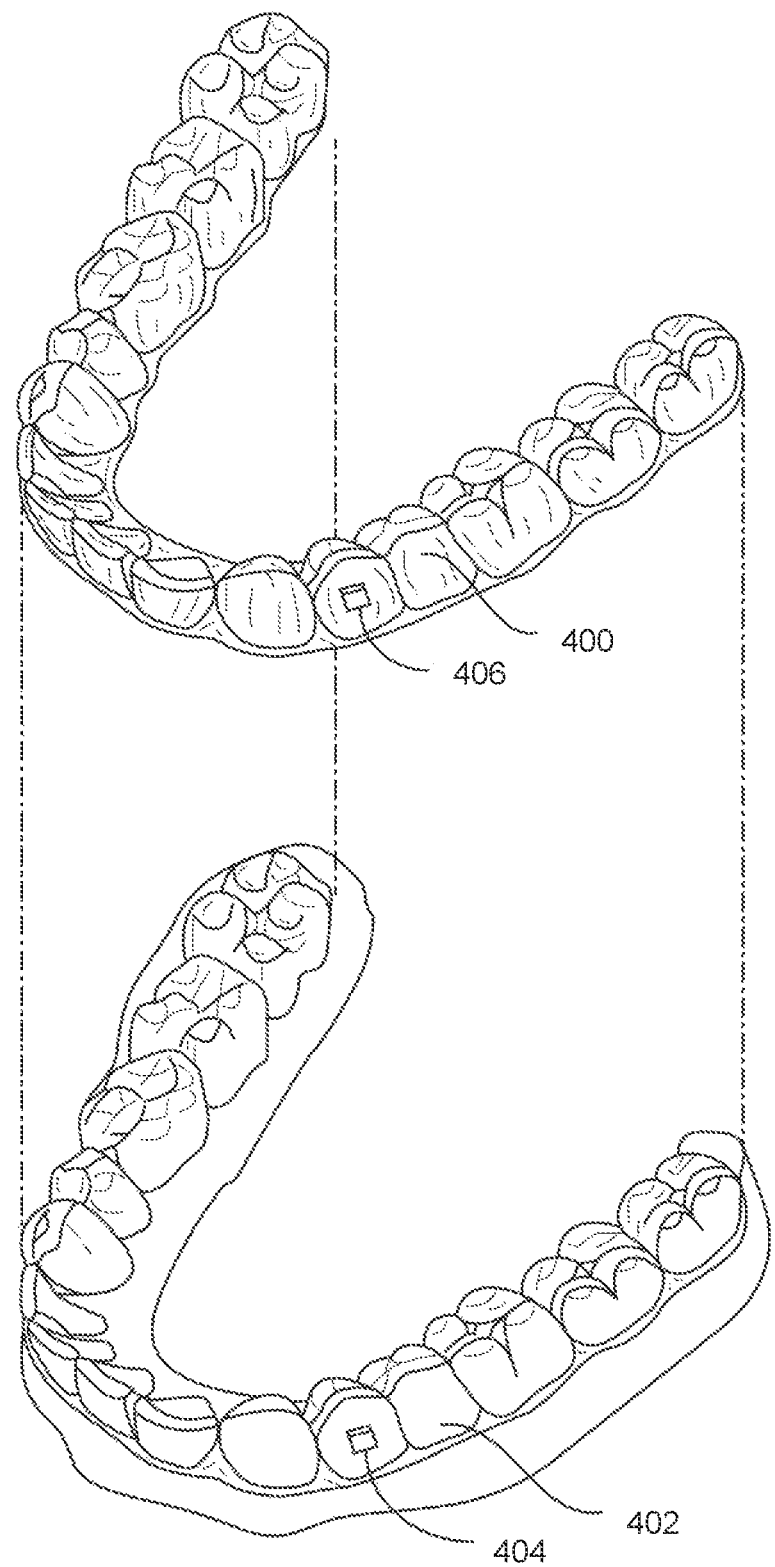
FIG. 9A illustrates a tooth repositioning appliance, in accordance with one or more embodiments herein.

FIG. 9A illustrates an exemplary tooth repositioning appliance or aligner 400 that can be worn by a patient in order to achieve an incremental repositioning of individual teeth 402 in the jaw. Such aligners may be used in or made by any of the methods described herein. The appliance can include a shell (e.g., a continuous polymeric shell or a segmented shell) having teeth-receiving cavities that receive and resiliently reposition the teeth. An appliance or portion(s) thereof may be indirectly fabricated using a physical model of teeth. For example, an appliance (e.g., polymeric appliance) can be formed using a physical model of teeth and a sheet of suitable layers of polymeric material. The physical model (e.g., physical mold) of teeth can be formed through a variety of techniques, including 3D printing. The appliance can be formed by thermoforming the appliance over the physical model. In some embodiments, a physical appliance is directly fabricated, e.g., using additive manufacturing techniques, from a digital model of an appliance. In some embodiments, the physical appliance may be created through a variety of direct formation techniques, such as 3D printing. An appliance can fit over all teeth present in an upper or lower jaw, or less than all of the teeth. The appliance can be designed specifically to accommodate the teeth of the patient (e.g., the topography of the tooth-receiving cavities matches the topography of the patient's teeth), and may be fabricated based on positive or negative models of the patient's teeth generated by impression, scanning, and the like. In some embodiments, the appliance can be a generic appliance configured to receive the teeth, but not necessarily shaped to match the topography of the patient's teeth. In some cases, only certain teeth received by an appliance will be repositioned by the appliance while other teeth can provide a base or anchor region for holding the appliance in place as it applies force against the tooth or teeth targeted for repositioning. In some cases, some or most, or even all, of the teeth will be repositioned at some point during treatment. Teeth that are moved can also serve as a base or anchor for holding the appliance as it is worn by the patient. In some embodiments, no wires or other means will be provided for holding an appliance in place over the teeth. In some cases, however, it may be desirable or necessary to provide individual attachments or other anchoring elements 404 on teeth 402 with corresponding receptacles or apertures 406 in the appliance 400 so that the appliance can apply a selected force on the tooth. Exemplary appliances, including those utilized in the Invisalign® System, are described in numerous patents and patent applications assigned to Align Technology, Inc. including, for example, in U.S. Pat. Nos. 6,450,807, and 5,975,893, as well as on the company's website, which is accessible on the World Wide Web (see, e.g., the url "invisalign.com"). Examples of tooth-mounted attachments suitable for use with orthodontic appliances are also described in patents and patent applications assigned to Align Technology, Inc., including, for example, U.S. Pat. Nos. 6,309,215 and 6,830,450.

Optionally, in cases involving more complex movements or treatment plans, it may be beneficial to utilize auxiliary components (e.g., features, accessories, structures, devices, components, and the like) in conjunction with an orthodontic appliance. Examples of such accessories include but are not limited to elastics, wires, springs, bars, arch expanders, palatal expanders, twin blocks, occlusal blocks, bite ramps, mandibular advancement splints, bite plates, pontics, hooks, brackets, headgear tubes, springs, bumper tubes, palatal bars, frameworks, pin-and-tube apparatuses, buccal shields, buccinator bows, wire shields, lingual flanges and pads, lip pads or bumpers, protrusions, divots, and the like. In some embodiments, the appliances, systems and methods described herein include improved orthodontic appliances with integrally formed features that are shaped to couple to such auxiliary components, or that replace such auxiliary components.

Figure 9B:
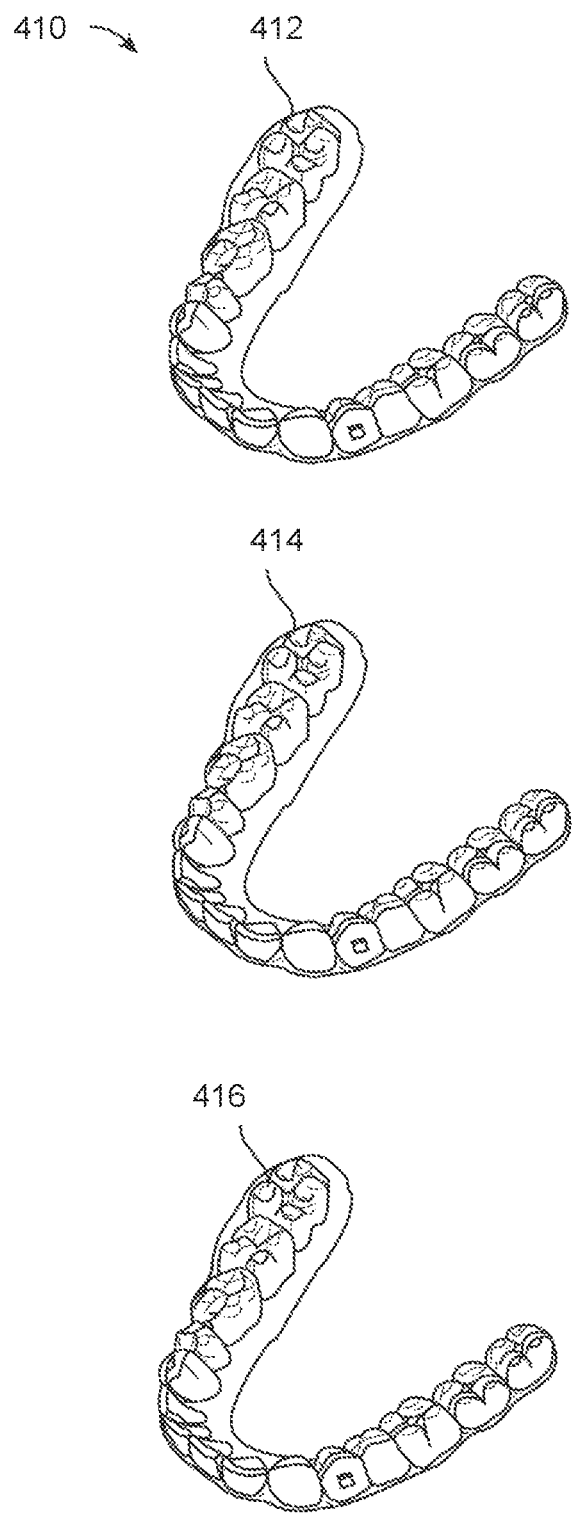
FIG. 9B illustrates a tooth repositioning system, in accordance with one or more embodiments herein.

FIG. 9B illustrates a tooth repositioning system 410 including a plurality of appliances 412, 414, 416. Any of the appliances described herein can be designed and/or provided as part of a set of a plurality of appliances used in a tooth repositioning system. Each appliance may be configured so a tooth-receiving cavity has a geometry corresponding to an intermediate or final tooth arrangement intended for the appliance. The patient's teeth can be progressively repositioned from an initial tooth arrangement towards a target tooth arrangement by placing a series of incremental position adjustment appliances over the patient's teeth. For example, the tooth repositioning system 410 can include a first appliance 412 corresponding to an initial tooth arrangement, one or more intermediate appliances 414 corresponding to one or more intermediate arrangements, and a final appliance 416 corresponding to a target arrangement. A target tooth arrangement can be a planned final tooth arrangement selected for the patient's teeth at the end of all planned orthodontic treatment. Alternatively, a target arrangement can be one of some intermediate arrangements for the patient's teeth during the course of orthodontic treatment, which may include various different treatment scenarios, including, but not limited to, instances where surgery is recommended, where interproximal reduction (IPR) is appropriate, where a progress check is scheduled, where anchor placement is best, where palatal expansion is desirable, where restorative dentistry is involved (e.g., inlays, onlays, crowns, bridges, implants, veneers, and the like), etc. As such, it is understood that a target tooth arrangement can be any planned resulting arrangement for the patient's teeth that follows one or more incremental repositioning stages. Likewise, an initial tooth arrangement can be any initial arrangement for the patient's teeth that is followed by one or more incremental repositioning stages.

Figure 10:
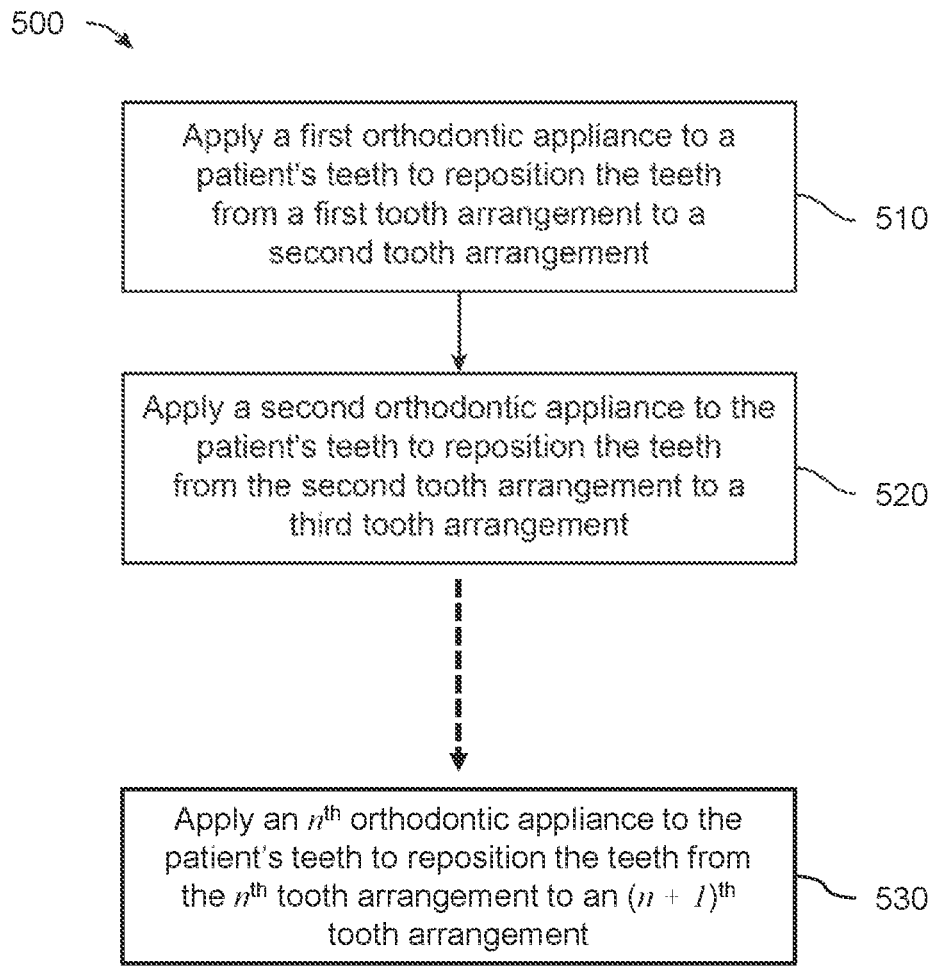
FIG. 10 illustrates a method of orthodontic treatment using a plurality of appliances, in accordance with one or more embodiments herein.

FIG. 10 illustrates a method 500 of orthodontic treatment using a plurality of appliances, in accordance with embodiments. The method 500 can be practiced using any of the appliances or appliance sets described herein. The appliance or the appliance set may be designed and/or optimized using any of the methods described herein. In block 510, a first orthodontic appliance is applied to a patient's teeth in order to reposition the teeth from a first tooth arrangement to a second tooth arrangement. In block 520, a second orthodontic appliance is applied to the patient's teeth in order to reposition the teeth from the second tooth arrangement to a third tooth arrangement. The method 500 can be repeated as necessary using any suitable number (n) and combination of sequential appliances in order to incrementally reposition the patient's teeth from an initial arrangement to a target arrangement, as illustrated in block 530. The appliances can be generated all at the same stage or in sets or batches (at the beginning of a stage of the treatment, at an intermediate stage of treatment, etc.), or the appliances can be fabricated one at a time, and the patient can wear each appliance until the pressure of each appliance on the teeth can no longer be felt or until the maximum amount of expressed tooth movement for that given stage has been achieved. A plurality of different appliances (e.g., a set) can be designed and even fabricated prior to the patient wearing any appliance of the plurality. After wearing an appliance for an appropriate period of time, the patient can replace the current appliance with the next appliance in the series until no more appliances remain. The appliances are generally not affixed to the teeth and the patient may place and replace the appliances at any time during the procedure (e.g., patient-removable appliances). The final appliance or several appliances in the series may have a geometry or geometries selected to overcorrect the tooth arrangement. For instance, one or more appliances may have a geometry that would (if fully achieved) move individual teeth beyond the tooth arrangement that has been selected as the "final." Such over-correction may be desirable in order to offset potential relapse after the repositioning method has been terminated (e.g., permit movement of individual teeth back toward their pre-corrected positions). Over-correction may also be beneficial to speed the rate of correction (e.g., an appliance with a geometry that is positioned beyond a desired intermediate or final position may shift the individual teeth toward the position at a greater rate). In such cases, the use of an appliance can be terminated before the teeth reach the positions defined by the appliance. Furthermore, over-correction may be deliberately applied in order to compensate for any inaccuracies or limitations of the appliance.

The various embodiments of the orthodontic appliances presented herein can be fabricated in a wide variety of ways. In some embodiments, the orthodontic appliances herein (or portions thereof) can be produced using direct fabrication, such as additive manufacturing techniques (also referred to herein as "3D printing) or subtractive manufacturing techniques (e.g., milling). In some embodiments, direct fabrication involves forming an object (e.g., an orthodontic appliance or a portion thereof) without using a physical template (e.g., mold, mask etc.) to define the object geometry.

In some embodiments, the orthodontic appliances herein can be fabricated using a combination of direct and indirect fabrication techniques, such that different portions of an appliance can be fabricated using different fabrication techniques and assembled in order to form the final appliance. For example, an appliance shell can be formed by indirect fabrication (e.g., thermoforming), and one or more structures or components as described herein (e.g., auxiliary components, power arms, etc.) can be added to the shell by direct fabrication (e.g., printing onto the shell).

The configuration of the orthodontic appliances herein can be determined according to a treatment plan for a patient, e.g., a treatment plan involving successive administration of a plurality of appliances for incrementally repositioning teeth. Computer-based treatment planning and/or appliance manufacturing methods can be used in order to facilitate the design and fabrication of appliances. For instance, one or more of the appliance components described herein can be digitally designed and fabricated with the aid of computer-controlled manufacturing devices (e.g., computer numerical control (CNC) milling, computer-controlled additive manufacturing such as 3D printing, etc.). The computer-based methods presented herein can improve the accuracy, flexibility, and convenience of appliance fabrication.

In some embodiments, computer-based 3D planning/design tools, such as Treat™ software from Align Technology, Inc., may be used to design and fabricate the orthodontic appliances described herein.

Figure 11:
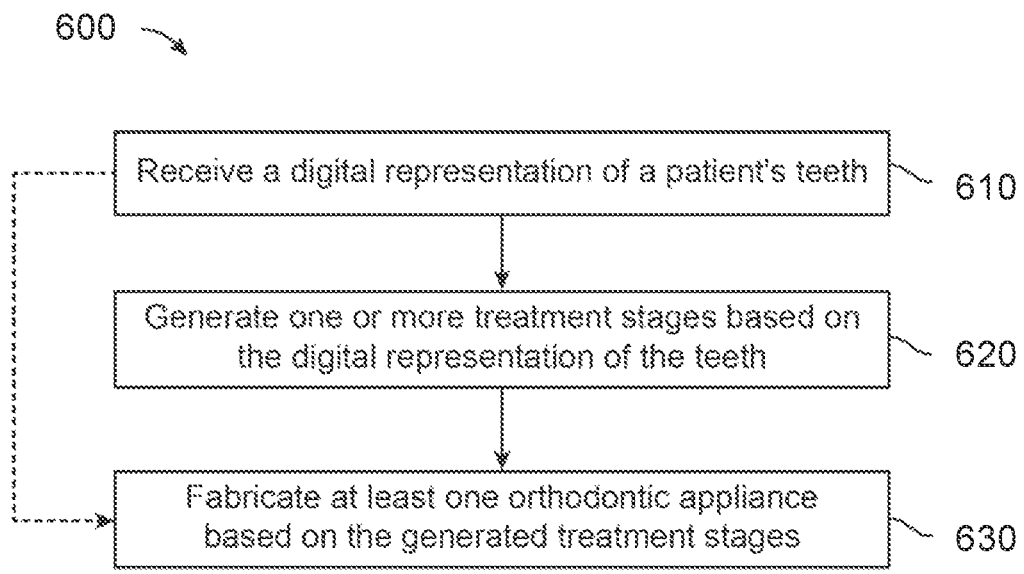
FIG. 11 illustrates a method for planning an orthodontic treatment, in accordance with one or more embodiments herein.

FIG. 11 illustrates a method 600 for digitally planning an orthodontic treatment and/or design or fabrication of an appliance, in accordance with embodiments. The treatment play may be validated using any of the methods described herein. The method 600 can be applied to any of the treatment procedures described herein and can be performed by any suitable data processing system.

In block 610, a digital representation of a patient's teeth is received. The digital representation can include surface topography data for the patient's intraoral cavity (including teeth, gingival tissues, etc.). The surface topography data can be generated by directly scanning the intraoral cavity, a physical model (positive or negative) of the intraoral cavity, or an impression of the intraoral cavity, using a suitable scanning device (e.g., a handheld scanner, desktop scanner, etc.). The digital representation may be obtained using the treatment plan gathering device 132 or may be retrieved from the treatment plan datastore 116, with respect to FIG. 1.

In block 620, one or more treatment stages are generated based on the digital representation of the teeth. The treatment stages can be incremental repositioning stages of an orthodontic treatment procedure designed to move one or more of the patient's teeth from an initial tooth arrangement to a target arrangement. For example, the treatment stages can be generated by determining the initial tooth arrangement indicated by the digital representation, determining a target tooth arrangement, and determining movement paths of one or more teeth in the initial arrangement necessary to achieve the target tooth arrangement. The movement path can be optimized based on minimizing the total distance moved, preventing collisions between teeth, avoiding tooth movements that are more difficult to achieve, or any other suitable criteria.

In block 630, at least one orthodontic appliance is fabricated based on the generated treatment stages. For example, a set of appliances can be fabricated, each shaped according to a tooth arrangement specified by one of the treatment stages, such that the appliances can be sequentially worn by the patient to incrementally reposition the teeth from the initial arrangement to the target arrangement. The appliance set may include one or more of the orthodontic appliances described herein. The fabrication of the appliance may involve creating a digital model of the appliance to be used as input to a computer-controlled fabrication system. The appliance can be formed using direct fabrication methods, indirect fabrication methods, or combinations thereof, as desired.

In some instances, staging of various arrangements or treatment stages may not be necessary for design and/or fabrication of an appliance. As illustrated by the dashed line in FIG. 11, design and/or fabrication of an orthodontic appliance, and perhaps a particular orthodontic treatment, may include use of a representation of the patient's teeth (e.g., receive a digital representation of the patient's teeth 610), followed by design and/or fabrication of an orthodontic appliance based on a representation of the patient's teeth in the arrangement represented by the received representation.

Optionally, some or all of the blocks of the method 600 are performed locally at the site where the patient is being treated and during a single patient visit, referred to herein as "chair side manufacturing." Chair side manufacturing can involve, for example, scanning the patient's teeth, automatically generating a treatment plan with treatment stages, and immediately fabricating one or more orthodontic appliance(s) to treat the patient using a chair side direct fabrication machine, all at the treating professional's office during a single appointment. In embodiments where a series of appliances are used to treat the patient, the first appliance may be produced chair side for immediate delivery to the patient, with the remaining appliances produced separately (e.g., off site at a lab or central manufacturing facility) and delivered at a later time (e.g., at a follow up appointment, mailed to the patient). Alternatively, the methods herein can accommodate production and immediate delivery of the entire series of appliances on site during a single visit. Chair side manufacturing can thus improve the convenience and speed of the treatment procedure by allowing the patient to immediately begin treatment at the practitioner's office, rather than having to wait for fabrication and delivery of the appliances at a later date. Additionally, chair side manufacturing can provide improved flexibility and efficiency of orthodontic treatment. For instance, in some embodiments, the patient is re-scanned at each appointment to determine the actual positions of the teeth, and the treatment plan is updated accordingly. Subsequently, new appliances can be immediately produced and delivered chair side to accommodate any changes to or deviations from the treatment plan.

Figure 12:
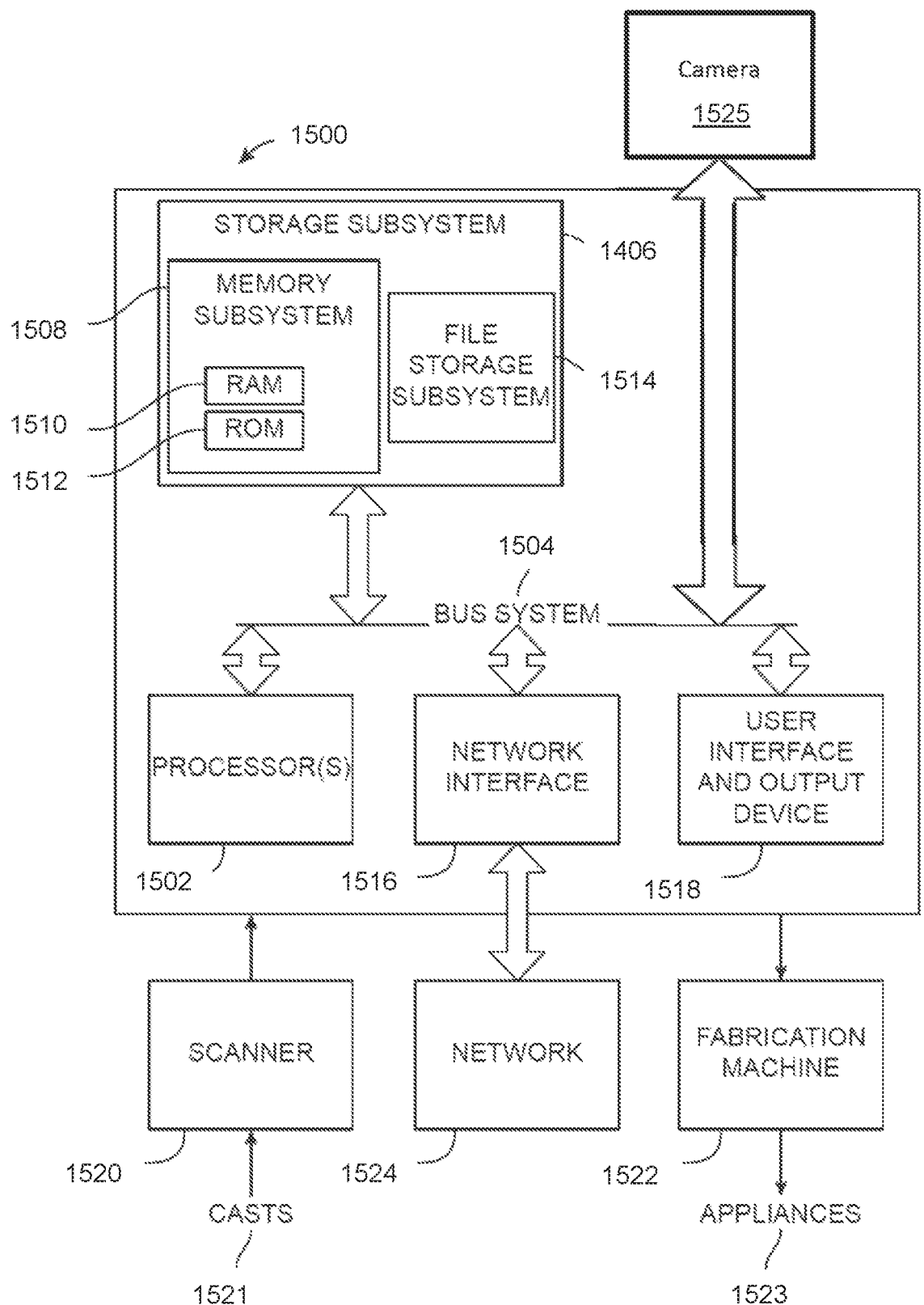
FIG. 12 depicts a simplified block diagram of a system for designing an orthodontic appliance and planning an orthodontic treatment, in accordance with one or more embodiments herein.

FIG. 12 is a simplified block diagram of a data processing system 1500 that may be used in executing methods and processes described herein. System 1500 describes the specialized hardware components comprising the computing device 130, with reference to FIG. 1. The data processing system 1500 typically includes at least one processor 1502 that communicates with one or more peripheral devices via bus subsystem 1504. These peripheral devices typically include a storage subsystem 1506 (memory subsystem 1508 and file storage subsystem 1514), a set of user interface input and output devices 1518, and an interface to outside networks 1516. This interface is shown schematically as "Network Interface" block 1516, and is coupled to corresponding interface devices in other data processing systems via communication network interface 1524. Data processing system 1500 can include, for example, one or more computers, such as a personal computer, workstation, mainframe, laptop, and the like.

The user interface input devices 1518 are not limited to any particular device, and can typically include, for example, a keyboard, pointing device, mouse, scanner, interactive displays, touchpad, joysticks, etc. Similarly, various user interface output devices can be employed in a system of the invention, and can include, for example, one or more of a printer, display (e.g., visual, non-visual) system/subsystem, controller, projection device, audio output, and the like.

Storage subsystem 1506 maintains the basic required programming, including computer readable media having instructions (e.g., operating instructions, etc.), and data constructs. The program modules discussed herein are typically stored in storage subsystem 1506. Storage subsystem 1506 typically includes memory subsystem 1508 and file storage subsystem 1514. Memory subsystem 1508 typically includes a number of memories (e.g., RAM 1510, ROM 1512, etc.) including computer readable memory for storage of fixed instructions, instructions and data during program execution, basic input/output system, etc. File storage subsystem 1514 provides persistent (non-volatile) storage for program and data files, and can include one or more removable or fixed drives or media, hard disk, floppy disk, CD-ROM, DVD, optical drives, and the like. One or more of the storage systems, drives, etc., may be located at a remote location, such coupled via a server on a network or via the internet/World Wide Web. In this context, the term "bus subsystem" is used generically so as to include any mechanism for letting the various components and subsystems communicate with each other as intended and can include a variety of suitable components/systems that would be known or recognized as suitable for use therein. It will be recognized that various components of the system can be, but need not necessarily be at the same physical location, but could be connected via various local-area or wide-area network media, transmission systems, etc.

Scanner 1520 includes any means for obtaining a digital representation (e.g., images, surface topography data, etc.) of a patient's teeth (e.g., by scanning physical models of the teeth such as casts 1521, by scanning impressions taken of the teeth, or by directly scanning the intraoral cavity), which can be obtained either from the patient or from treating professional, such as an orthodontist, and includes means of providing the digital representation to data processing system 1500 for further processing. Scanner 1520 may be located at a location remote with respect to other components of the system and can communicate image data and/or information to data processing system 1500, for example, via a network interface 1524. Fabrication system 1522 fabricates appliances 1523 based on a treatment plan, including data set information received from data processing system 1500. Fabrication machine 1522 can, for example, be located at a remote location and receive data set information from data processing system 1500 via network interface 1524. The camera 1525 may include any image capture device configured to capture still images or movies. The camera 1525 may facilitate capturing various perspectives of a patient's dentition. In some implementations, the camera 1525 may facilitate capture of images at various focal lengths and distances from the patient.

The data processing aspects of the methods described herein can be implemented in digital electronic circuitry, or in computer hardware, firmware, software, or suitable combinations thereof. Data processing apparatus can be implemented in a computer program product tangibly embodied in a machine-readable storage device for execution by a programmable processor. Data processing blocks can be performed by a programmable processor executing program instructions to perform functions by operating on input data and generating output. The data processing aspects can be implemented in one or more computer programs that are executable on a programmable system, the system including one or more programmable processors operably coupled to a data storage system. Generally, a processor will receive instructions and data from a read-only memory and/or a random access memory. Storage devices suitable for tangibly embodying computer program instructions and data include all forms of nonvolatile memory, such as: semiconductor memory devices, such as EPROM, EEPROM, and flash memory devices; magnetic disks such as internal hard disks and removable disks; magneto-optical disks; and CD-ROM disks.

Although the detailed description contains many specifics, these should not be construed as limiting the scope of the disclosure but merely as illustrating different examples and aspects of the present disclosure. It should be appreciated that the scope of the disclosure includes other embodiments not discussed in detail above. Various other modifications, changes and variations which will be apparent to those skilled in the art may be made in the arrangement, operation and details of the methods, systems, and apparatus of the present disclosure provided herein without departing from the spirit and scope of the invention as described herein. While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method of mapping mechanical interactions, the method comprising:
   (a) generating an orthodontic treatment plan to move a patient's teeth from an initial position toward a final position, the treatment plan comprising a first stage and a second stage;
   (b) building a 3D model of an orthodontic appliance at the second stage;
   (c) building a 3D model of the patient's teeth at the first stage;
   (d) mapping spatial differences between the 3D model of the orthodontic appliance at the second stage and the 3D model of the patient's teeth at the first stage;
   (e) evaluating mechanical interactions of the orthodontic appliance at the second stage with the patient's teeth at the first stage, wherein the evaluating is based at least in part on the mapped spatial differences; and
   (f) mapping forces applied by the orthodontic appliance at the second stage to each tooth of the patient's teeth at the first stage, wherein the mapping of the applied forces is based at least in part on the evaluated mechanical interactions.

2. The method of claim 1, wherein the first stage and the second stage are consecutive stages.

3. The method of claim 1, wherein the first stage is the initial position and the second stage is the final position.

4. The method of claim 1, wherein the 3D model of the patient's teeth is generated using a scanning system.

5. The method of claim 1, further comprising determining if the forces applied match predicted forces from the orthodontic treatment plan.

6. The method of claim 1, further comprising modifying the treatment plan based at least in part on the mapped forces.

7. The method of claim 1, further comprising repeating (a)-(f).

8. The method of claim 1, further comprising creating a 3D force displacement model of the evaluated mechanical interactions between 3D model of the orthodontic appliance and the 3D model of the patient's teeth, wherein in (f), the mapping of the applied forces is based at least in part on the 3D force displacement model.

9. A method of mapping tooth movements, the method comprising:
   (a) generating an orthodontic treatment plan to move a patient's teeth from an initial position toward a final position, the treatment plan comprising a first stage and a second stage;
   (b) building a first 3D model of the patient's teeth at the first stage and a second 3D model of the patient's teeth at the second stage;
   (c) building a first 3D model of a first neutral aligner at the first stage and second 3D model of a second neutral aligner at the second stage;
   (d) mapping spatial differences between second 3D model of the second neutral aligner at the second stage and first 3D model of the first neutral aligner at the first stage;
   (e) evaluating mechanical interactions of the second neutral aligner at the second stage with the patient's teeth at the first stage, that corresponds to the first 3D model of the first neutral aligner at the first stage, wherein the evaluating is based at least in part on the mapped spatial differences; and
   (f) mapping forces applied by the second neutral aligner at the second stage to each tooth of the patient's teeth at the first stage, wherein the mapping of the applied forces is based at least in part on the evaluated mechanical interacts.

10. The method of claim 9, wherein the first stage and the second stage are consecutive.

11. The method of claim 9, wherein the first stage is the initial position and the second stage is the final position.

12. The method of claim 9, wherein the first and second 3D models of the patient's teeth are generated using a scanning system.

13. The method of claim 9, further comprising determining if the forces applied match predicted forces from the orthodontic treatment plan.

14. The method of claim 9, further comprising modifying the treatment plan based at least in part on the mapped forces.

15. The method of claim 9, further comprising repeating (a)-(f).

16. The method of claim 9, further comprising creating a 3D force displacement model of the evaluated mechanical interactions between 3D model of the orthodontic appliance and the 3D model of the patient's teeth, wherein in (f), the mapping of the applied forces is based at least in part on the 3D force displacement model.

* * * * *